(12) United States Patent
Poliner et al.

(10) Patent No.: US 11,861,969 B2
(45) Date of Patent: Jan. 2, 2024

(54) VOLUME AND TIME EFFICIENT SMART DISPENSING SYSTEMS

(71) Applicant: POLYTEX TECHNOLOGIES LTD., Caesarea (IL)

(72) Inventors: Tomer Poliner, Caesarea (IL); Reuven Zander, Caesarea (IL)

(73) Assignee: POLYTEX TECHNOLOGIES LTD., Caesarea (IL)

( * ) Notice: Subject to any disclaimer, the term of this patent is extended or adjusted under 35 U.S.C. 154(b) by 178 days.

(21) Appl. No.: 17/527,464

(22) Filed: Nov. 16, 2021

(65) Prior Publication Data

US 2022/0157111 A1   May 19, 2022

Related U.S. Application Data

(60) Provisional application No. 63/115,704, filed on Nov. 19, 2020, provisional application No. 63/115,698, filed on Nov. 19, 2020.

(51) Int. Cl.
*G07F 11/60* (2006.01)
*G07F 11/16* (2006.01)
*A61L 2/10* (2006.01)
*A61L 2/12* (2006.01)
*G07F 11/72* (2006.01)

(52) U.S. Cl.
CPC .............. *G07F 11/165* (2013.01); *A61L 2/10* (2013.01); *A61L 2/12* (2013.01); *G07F 11/60* (2013.01); *G07F 11/72* (2013.01); *A61L 2202/122* (2013.01)

(58) Field of Classification Search
CPC ..................................................... G07F 11/065
See application file for complete search history.

(56) References Cited

U.S. PATENT DOCUMENTS

| 4,889,210 | A | * | 12/1989 | Alcaraz | G07F 9/10 |
| | | | | | 901/50 |
| 5,143,193 | A | * | 9/1992 | Geraci | G07F 7/069 |
| | | | | | 414/277 |
| 6,006,946 | A | * | 12/1999 | Williams | G07F 17/0092 |
| | | | | | 221/9 |
| 7,474,938 | B2 | | 1/2009 | Poliner | |
| 8,875,942 | B2 | | 11/2014 | Poliner | |
| 2013/0103198 | A1 | * | 4/2013 | Nakamoto | A23G 9/288 |
| | | | | | 700/257 |
| 2014/0120235 | A1 | * | 5/2014 | Jones | G07F 17/0064 |
| | | | | | 901/30 |
| 2018/0204408 | A1 | * | 7/2018 | Lin | G07F 11/005 |

FOREIGN PATENT DOCUMENTS

EP           2378495 A1    10/2011

* cited by examiner

*Primary Examiner* — Gene O Crawford
*Assistant Examiner* — Ayodeji T Ojofeitimi
(74) *Attorney, Agent, or Firm* — The Roy Gross Law Firm, LLC; Roy Gross

(57) ABSTRACT

Provided herein are automated time and space efficient item dispensing systems having a plurality of storage compartments and one or more adjustable grippers, for fast and accurate automatic dispensing of items or sets of items.

28 Claims, 15 Drawing Sheets

VOLUME AND TIME EFFICIENT SMART DISPENSING SYSTEMS

CROSS REFERENCE TO RELATED APPLICATIONS

This application claims priority to U.S. Provisional Patent Application Nos. 63/115,698 filed on Nov. 19, 2020 and 63/115,704 filed on Nov. 19, 2020. The contents of the above applications are all incorporated by reference in their entirety.

TECHNICAL FIELD

The present disclosure relates generally to time and volume efficient dispensing systems, having one or more adjustable grippers, configured to operate independently and concurrently to dispense items or sets of items.

BACKGROUND

Automated dispensing machines, for example, vending machines, are used to automatically dispense and/or collect various items and articles, such as clothing, towels, food items, beverages, newspapers, and the like. The size and the mode of operation of a dispensing machine may vary based on its intended use and the type of items dispensed (and returned). For example, clothes dispensing machines may include suitable mechanical means for grasping, conveying, and dispensing a clothing item(s) selected by a user, e.g. via a user interface on the clothes dispensing machine. Some clothes dispensing systems may further allow the return of used items. For example, U.S. Pat. No. 7,474,938 is directed to an interactive automated article dispensing system, while U.S. Pat. No. 8,875,942 is directed to a side-grip method for grasping textile items in a vending machine. Publication EP 2378495 is directed to vending machines for flexible products, particularly of the type of clothes and textile items in general.

Nevertheless, there is a need in the art for improved dispensing systems, which are fast, efficient, time-saving and environmentally friendly, which can accommodate a wide range of items that can be dispensed using one or more adjustable grippers that are capable of dispensing various types of items in an efficient manner, and allowing dispensing of sets of items to a user, in a fast and accurate manner.

SUMMARY

Aspects of the disclosure, according to some embodiments thereof, relate to advantageous items dispensing systems which are space saving, cost and time efficient and which can accommodate a large variety of items and dispense the variety of items or sets of items in a fast and accurate manner.

According to some embodiments, the dispensing systems disclosed herein include a plurality of variable shelves/compartments, which are configured to laterally move (in a direction from front face of the system towards the back face of the system), along an axis (separately or in conjunction), in the direction of an adjustable gripper, wherein the adjustable gripper is configured to grip an item from a respective compartment at an adjustable spatial location thereof and/or at an adjustable gripping tense/strength, according to characteristics of the dispensed item. Utilizing such advantageous settings, enhanced item dispensing is achieved by reducing dispensing time, increasing dispensing accuracy and further increasing dispensing quality, by allowing item-adjusted gripping. Additionally, utilizing such advantageous settings provides dispensing systems which are user friendly, cost effective and environmentally friendly by consuming less energy, requiring less space, produce lower level of noise, have larger capacity, while allowing an increased variety of items to be dispensed.

According to some embodiments, the dispensing systems disclosed herein advantageously allow occupying lower space while maintaining enhanced items dispensing rates and increased dispensing accuracy. According to some embodiments, the systems disclosed herein allow accommodating a wide range of items to be dispensed, wherein the items can be successfully dispensed utilizing an adjustable gripper, configured to grip an item at an adjustable position and/or strength/tense based on the type/characteristics of the item to be dispensed.

According to some embodiments, the systems disclosed herein are further advantageous as they can further optionally include a disinfection/cleaning unit, thereby ensuring that the dispensed items are disinfected and/or clean. This is of particular importance for environments requiring at least some degree of sterility (such as, for example, items used in surgical procedures) and/or at least some degree of cleanliness (such as, for example, clean rooms).

According to some embodiments, the systems disclosed herein may further utilize artificial intelligence tools to allow for automatic identification of quality and/or quantity of dispensed and/or returned textile items. Consequently, systems of the present disclosure allow for real-time management of inventory.

Thus, according to an aspect of some embodiments, there is provided an item dispensing system which includes: a container having a front face and a back face, the container includes a plurality of storage compartments/cells configured for storage/holding of items, wherein the storage compartments are arranged in one or more sets, each set is arranged in rows and/or columns, wherein each of the sets of the storage compartments is configured to move laterally between the front face and the back face of the container; and a gripper assembly, configured to move along a vertical axis and/or a horizontal axis, said gripper assembly includes at least one adjustable gripper, configured to allow an adjustable gripping of an item in a designated storage compartment and deliver the gripped item to a dispensing outlet (for example, via a chute), wherein the lateral movement of the set of compartments and the vertical and/or horizontal movement of the gripper assembly is coordinated to allow temporal and spatial positioning of the adjustable gripper and the designed compartment.

According to some embodiments, there is provided an item dispensing system including: a container having a front face and a back face, the container includes: a plurality of storage compartments configured for storage/holding of items, wherein the storage compartments are arranged in one or more sets, each set is arranged in rows and/or columns, wherein each of the sets of the storage compartments is configured to move laterally between the front face and the back face of the container, and a gripper assembly configured to move along a vertical axis and/or a horizontal axis, the gripper assembly includes at least one adjustable gripper configured to allow an adjustable gripping of an item in a designated storage compartment and deliver the gripped item to a dispensing outlet, wherein the lateral movement of the set of compartments and the movement of the gripper assembly is coordinated to thereby allow temporal and spatial accurate positioning of the adjustable gripper and the designed compartment.

According to some embodiments of the present invention, there is provided an item dispensing system including: a container having a front face and a back face, the container includes: a plurality of storage compartments configured for storage/holding of items, wherein the storage compartments are arranged in one or more stationary sets, each set is arranged in rows and/or columns, wherein each of the sets of the storage compartments is placed in a varying distance from the back face of the container, and a gripper assembly configured to move along a vertical axis and/or a horizontal axis, the gripper assembly includes at least one adjustable gripper configured to allow an adjustable gripping of an item in a designated storage compartment and deliver the gripped item to a dispensing outlet, wherein the vertical and/or horizontal movement of the gripper assembly is configured to position the adjustable gripper over the designed compartment to allow the adjustable gripping of the item.

According to some embodiments, the adjustable gripper includes at least two opposing movable arms, configured to adjustably grip an item, based on the characteristics of the item in the compartment. According to some embodiments, the characteristics of the item includes one or more of: type of item, size of item, weight of item, packaging of item, folding condition of item, number of items in a compartment, location of the item in the compartment, or any combination thereof.

According to some embodiments, the adjustable gripping of the item includes a gripping location/position of the item and/or the strength/tense of gripping. According to some embodiments, the gripper assembly is located in close proximity to the back face of the container. According to some embodiments, the degree of lateral movement of the set of compartments is at least partially based on the characteristic of items in the respective compartments.

According to some embodiments, the larger the item, the set of compartments is configured to laterally move closer to the back face of the container. According to some embodiments, a coordinated movement of the gripper assembly and the set of compartments includes a synchronized movement or a sequential movement. According to some embodiments, the compartment size is adjustable, to allow precise accommodation of various types of items.

According to some embodiments, one or more of the compartments includes one or more sensors configured to provide indications regarding inventory of items. According to some embodiments, the system further includes at least one RF ID reader. According to some embodiments, the RF ID reader includes an RF ID antenna positioned in close proximity to the dispensing outlet, configured to detect/identify a corresponding RF ID Tag of a dispensed item.

According to some embodiments, the system further includes an internal collection chamber configured to collect items that were gripped but were not dispensed via the dispensing outlet. According to some embodiments, items that were gripped but were not dispensed include: damaged items, items having a defective RF ID tag, Items missing an RF ID tag, multiple gripped items, or any combination thereof.

According to some embodiments, the system further includes a disinfecting and/or cleaning unit. According to some embodiments, the disinfecting and/or cleaning unit includes one or more of: a UV disinfection unit, a microwave disinfecting unit, a vacuum unit, an air circulation unit, or any combination thereof. According to some embodiments, the system further includes a lower back collecting chamber, configured to collect items that have been misplaced or fallen from compartments.

According to some embodiments, the sets of compartments are arranged at a varying distance from the back face of the container. According to some embodiments, the system further includes a user interface unit. According to some embodiments, the system further includes one or more motors, one or more controllers, one or more processors, or combinations thereof. According to some embodiments, the system further includes a communication unit.

According to some embodiments, the system may be functionally or physically associated with an item return unit. According to some embodiments, the return unit may include a compactor, configured to compress returned items within the return unit, to thereby increase capacity of the return unit. In some embodiments, operation of the compactor may be controlled by a processor, based on information obtained from one or more sensors indicative of amount, number, size and/or weight of returned items. In some embodiments, the compactor may be operated manually. In some embodiments, the compactor may be operated periodically.

According to some embodiments, the front face of the container and/or the second face of the container are configured to at least partially open, to allow placement of items in one or more compartments from a respective front side and/or a respective back side of the container. According to some embodiments, the items are selected from flexible products, textile, newspapers, clothing, bed linen, tablecloths, towels, or any combination thereof. According to some embodiments, the clothing items includes garments, pants, shirts, scrubs, dress, skirts, socks, underwear, bathrobes, or any combination thereof.

According to some embodiments of the present invention there is provided a method for dispensing an item from an item dispensing system, the method includes: (a) providing an item dispensing system including: a container having a front face and a back face, the container includes: a plurality of storage compartments configured for storage/holding of items, wherein the storage compartments are arranged in sets, wherein each of the sets of the storage compartments is configured to move laterally between the front face and the back face of the container, and a gripper assembly configured to move along a vertical axis and/or a horizontal axis, the gripper assembly includes at least one adjustable gripper configured to allow an adjustable gripping of an item in a designated storage compartment, and deliver the gripped item to a dispensing outlet; and (b) selecting an item for dispensing using a user interface of the system, wherein, based on the selected item, the lateral movement of the set of compartments and the horizontal and/or vertical movement of the gripper assembly is coordinated to allow temporal and spatial positioning of the adjustable gripper and the designed compartment including the selected item, to thereby allow the adjustable gripper to adjustably grip the selected item and deliver the selected item to the dispensing outlet.

According to some embodiments, the adjustable gripper includes at least two opposing movable arms, configured to adjustably grip the selected item, based on the characteristics of the selected item in the compartment. According to some embodiments, the characteristics of the selected item includes one or more of: type of item, size of item, weight of item, packaging of item, folding condition of item, number of items in a compartment, location of the item in the compartment, or any combination thereof.

According to some embodiments, the adjustable gripping of the item includes a gripping location/position of the item and/or the strength/tense of gripping. According to some embodiments, the degree of lateral movement of the set of compartments is based on the characteristic of items in the respective compartments. According to some embodiments, a coordinated movement of the gripper assembly and the set of compartments includes a synchronized movement.

According to some embodiments, the method further includes sensing indications regarding inventory of items, based on information obtained from one or more sensors located in one or more compartments. According to some embodiments, the method may further include detecting RFID signal emitted by an RFID tag of a dispensed item. According to some embodiments, the method may further include detecting RF ID signals emitted by RF ID tags of one or more stored items. According to some embodiments, the method further includes collecting items that were gripped but were not dispensed via the dispensing outlet in an internal collection chamber.

According to some embodiments, the method further includes disinfecting and/or cleaning an interior space/volume of the container. According to some embodiments, the disinfecting and/or cleaning includes one or more of: UV disinfecting, microwave disinfecting, vacuuming, circulating air, or any combination thereof. According to some embodiments, the method further includes collecting items that have been misplaced or fell from compartments in a lower back collecting chamber.

According to some embodiments, the method further includes placing a one or more stocks of items in one or more compartments from a front side opening of the container and/or from a back side opening of the container. According to some embodiments, the items are selected from flexible products, textile, newspapers, clothing, bed linen, tablecloths, towels, garments, pants, shirts, scrubs, dress, skirts, socks, underwear, bathrobes or any combination thereof.

According to some embodiments, the dispensing systems disclosed herein include at least two gripper units, each may operate independently, to allow the gripping of at least two separate items (set of items), and the concurrent dispensing of the sets of items to a user, resulting in improved overall dispensing time.

According to some embodiments, the gripper units are configured to operate in synchronization, in simultaneous, or semi simultaneous manner (for example, concurrently) to grip desired items, and to allow dispensing of the gripped items in a concurrent manner, i.e., the gripped items are dispensed together, at the same time and/or approximately/essentially at the same time.

According to some embodiments, the gripper units are configured to at least partially overlap in their operation. In some embodiments, the operation time of the gripper units at least partially overlap, such that for at least a portion of the duration of operation of the gripper units, all the gripper units (such as two or more) are operating.

According to some embodiments, the dispensing systems disclosed herein advantageously allow enhanced dispensing rates of sets of items, as well as increased dispensing accuracy, as further detailed below.

According to some embodiments, the systems disclosed herein are further advantageous as they may further optionally include a disinfection/cleaning unit, thereby ensuring that the dispensed items are disinfected and/or clean. This is of particular importance for environments requiring at least some degree of sterility (such as, for example, items used in surgical procedures) and/or at least some degree of cleanliness (such as, for example, clean rooms).

According to some embodiments of the present invention there is provided an item dispensing system, including: a plurality of storage compartments configured for storage/holding of items, wherein the storage compartments are arranged in rows and/or columns, at least two gripper units configured to move along at least one axis, each of the gripper units being configured to grip an item positioned within a designated storage compartment and deliver the gripped item to a dispensing outlet of the item dispensing system, wherein the at least one axis and/or one of the at least two gripper units are configured such that the at least two gripper units are independently operable, thereby allowing concurrent dispensing of two or more items, wherein each of the items originates from a separate designated storage compartment.

According to some embodiments, the grippers are concurrently movable along the at least one axis. According to some embodiments, the grippers are consecutively movable along the at least one axis. According to some embodiments, the grippers are moveably coupled to the at least one axis. According to some embodiments, the at least one axis includes at least one horizontal axis and/or at least one vertical axis.

According to some embodiments, the system includes a processor and a driving unit in communication with the processor, wherein the driving unit is coupled to the at least two grippers and the processor is configured to control a movement of the at least two grippers by controlling an operation of the driving unit. According to some embodiments, the processor is configured to operate the at least two grippers simultaneously. According to some embodiments, the processor is configured to calculate an operation rout for two or more gripper units simultaneously.

According to some embodiments, the system includes a user interface module configured to receive input from a user associated with a specified item to be dispensed, and where the processor is configured to identify a storage unit containing the specified item. According to some embodiments, the system further includes a disinfecting and/or cleaning unit. According to some embodiments, the disinfecting and/or cleaning unit includes one or more of: a UV disinfection unit, a microwave disinfecting unit, a vacuum unit, an air circulation unit, or any combination thereof.

According to some embodiments, the storage compartments may be arranged in one or more stationary sets, each set is arranged in rows and/or columns, wherein each of the sets of the storage compartments is placed in a varying distance from a back face of a container comprising said storage compartments.

According to some embodiments, the item dispensing system may be functionally or physically associated with an item return unit. T According to some embodiments, the return unit comprises a compactor, configured to compress returned items within the return unit.

According to some embodiments of the present invention there is provided a method for simultaneously dispensing a plurality of items from an item dispensing system, including: identifying a plurality of storage compartments associated with two or more items, wherein each of the identified storage compartments is associated with one or more of the plurality of items, moving two or more gripper units to the plurality of identified storage compartments, removing one or more items from the identified storage compartments, dispensing the items, using the two or more gripper units, through a dispensing outlet, wherein an operation of the two or more gripper units is coordinated such that one or more of the identifying, the moving, the removing, and the dispensing associated with a first item of the plurality of items is simultaneous with at least one of the identifying, the moving, the removing, and the dispensing associated with a second item of the plurality of items.

According to some embodiments, the method may further include receiving one or more signals indicative of the plurality of items. According to some embodiments, the method further includes adjusting at least one of the gripper units, based, at least in part, on the type of one of the plurality of items. According to some embodiments, the method includes calculating a route for the two or more gripper units such that the plurality of items may be dispensed simultaneously. According to some embodiments, the method includes moving the two or more gripper units along a same axis of movement.

According to some embodiments, the method includes moving the two or more gripper units along two or more different axes of movement. According to some embodiments, the method includes moving the two or more gripper units independently of each other. According to some embodiments, the method further includes disinfecting and/or cleaning an interior space/volume of the container. According to some embodiments, the disinfecting and/or cleaning includes one or more of: UV disinfecting, microwave disinfecting, vacuuming, circulating air, or any combination thereof.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not drawn to scale. Moreover, two different objects in the same figure may be drawn to different scales. In particular, the scale of some objects may be greatly exaggerated as compared to other objects in the same figure.

In block diagrams and flowcharts, optional elements/components and optional stages may be included within dashed boxes.

In the figures:

Figure 1:
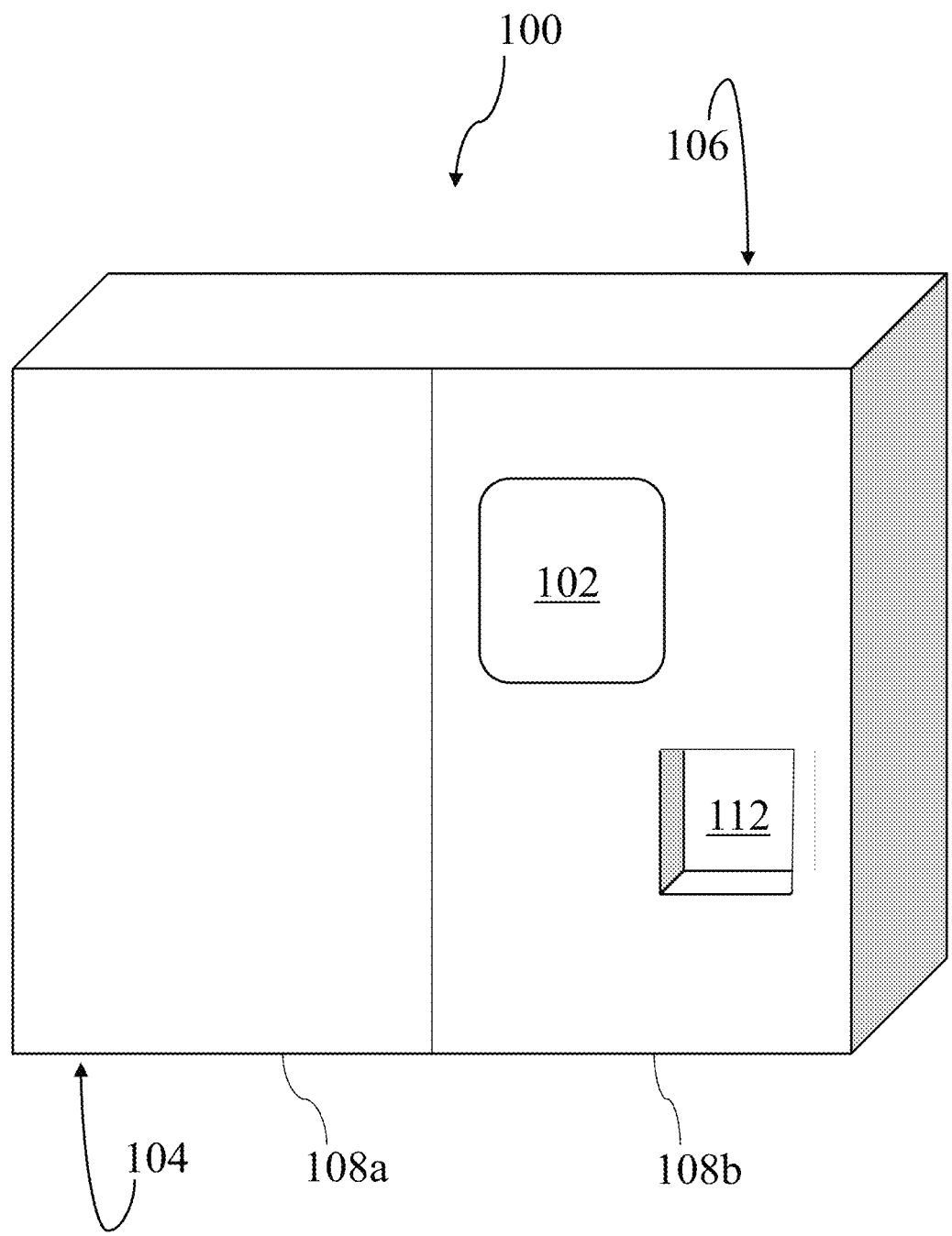
Figure 2:
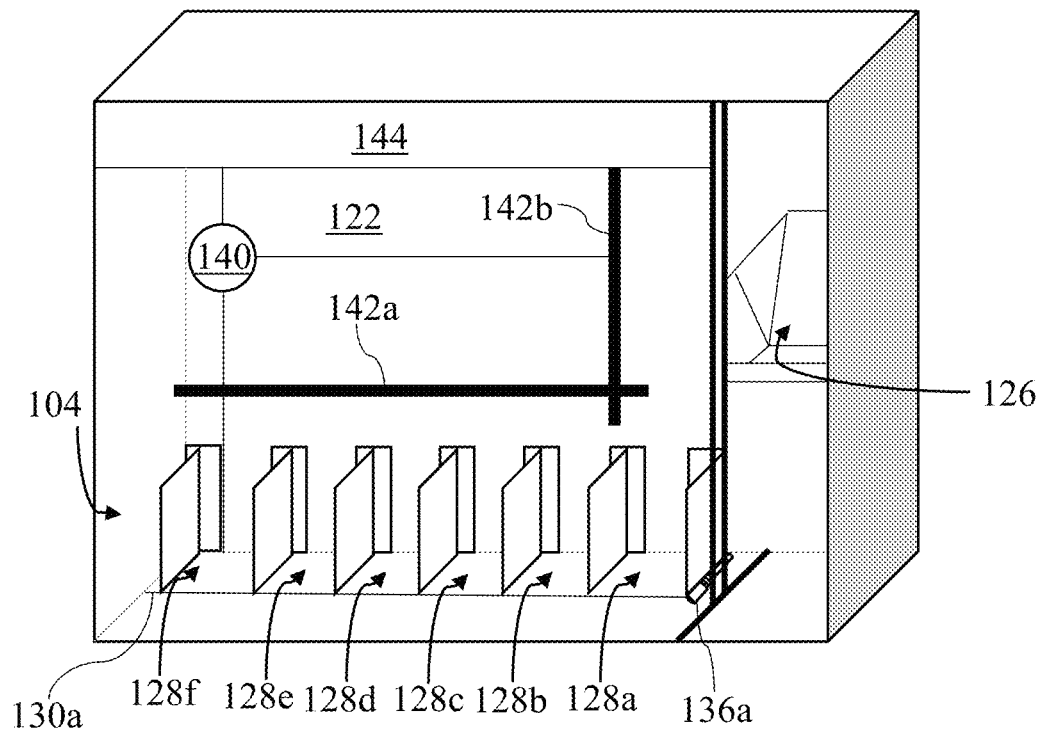
Figure 3:
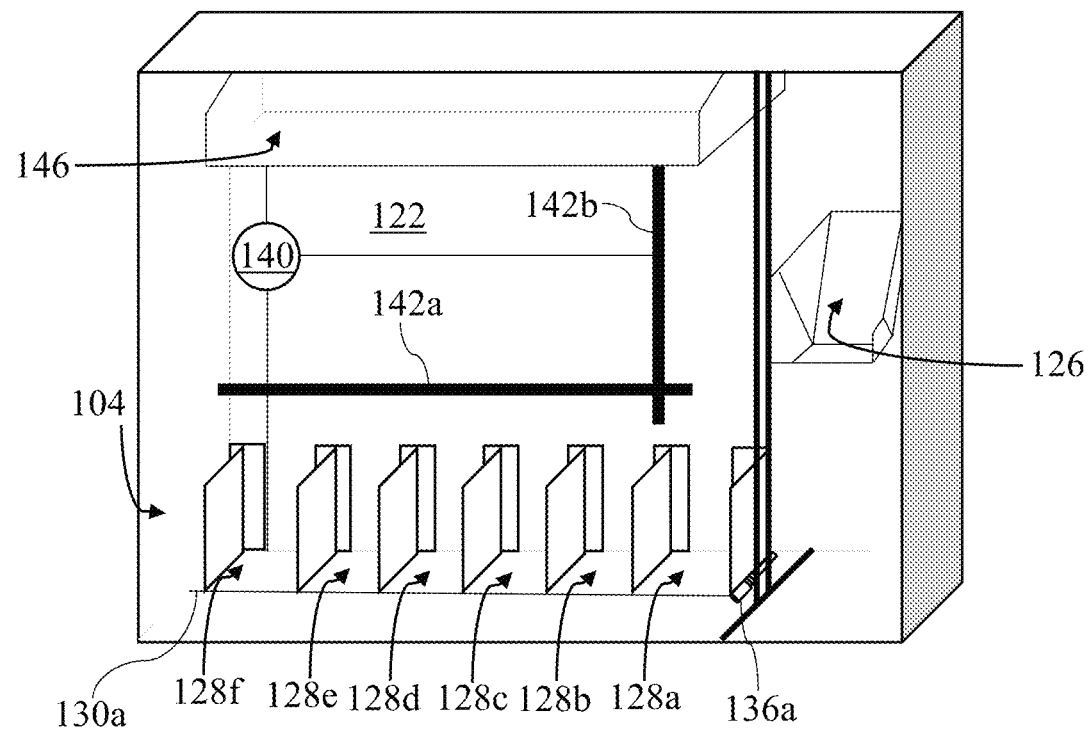
Figure 4:
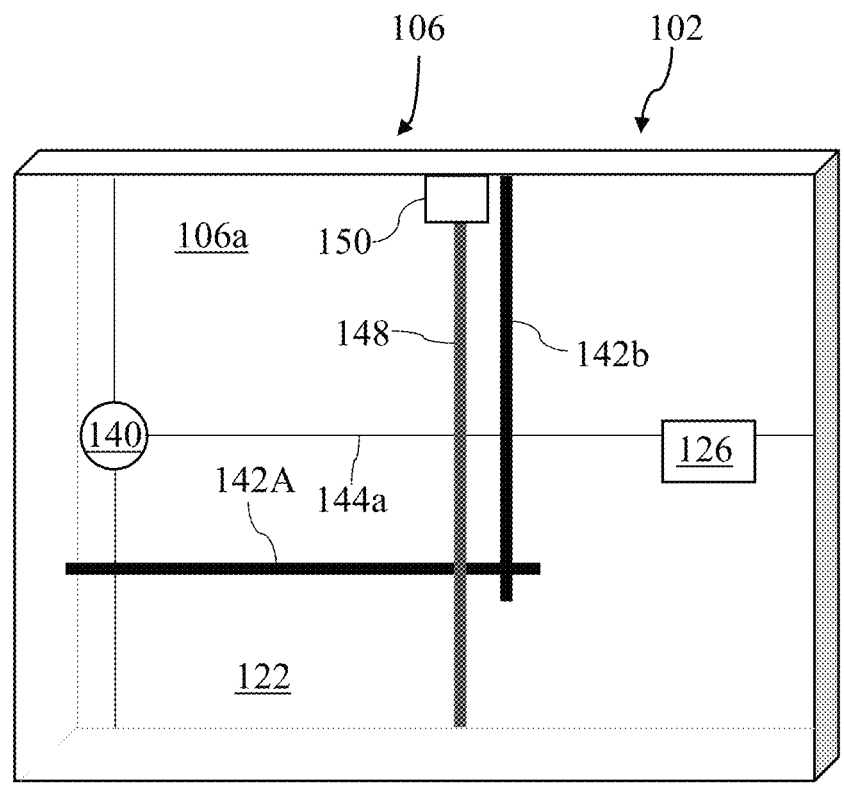
Figure 5A:
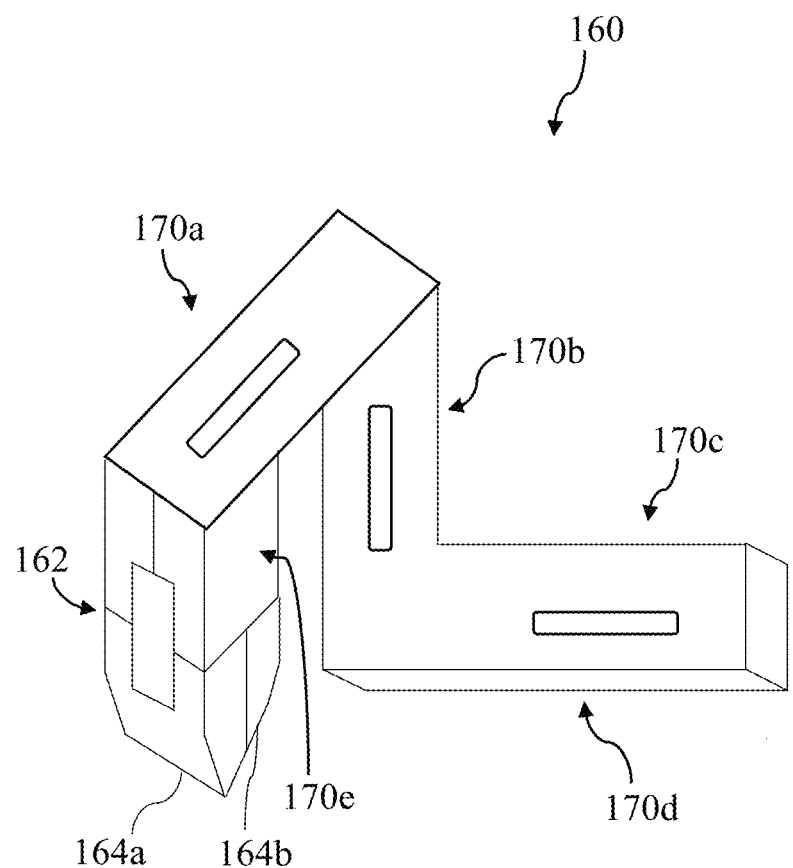
Figure 5B:
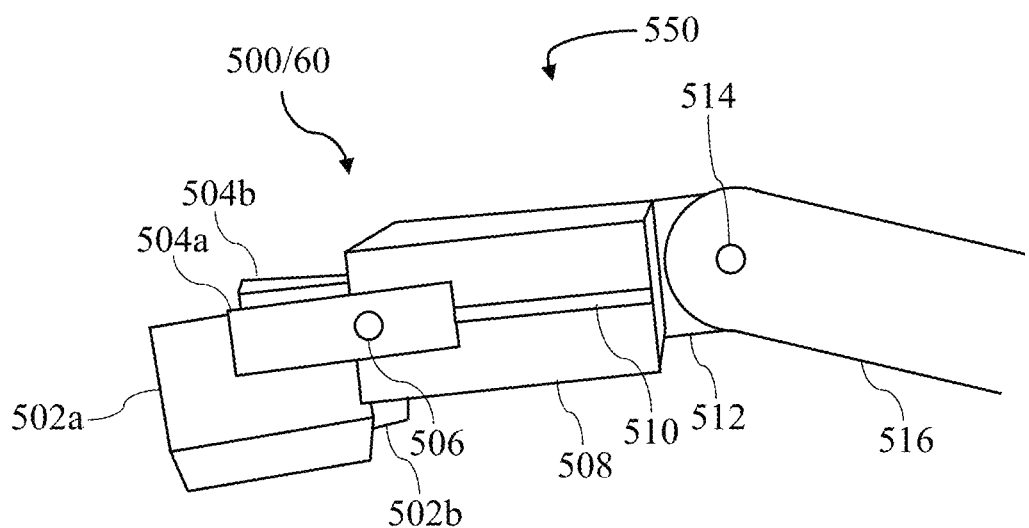
Figure 5C:
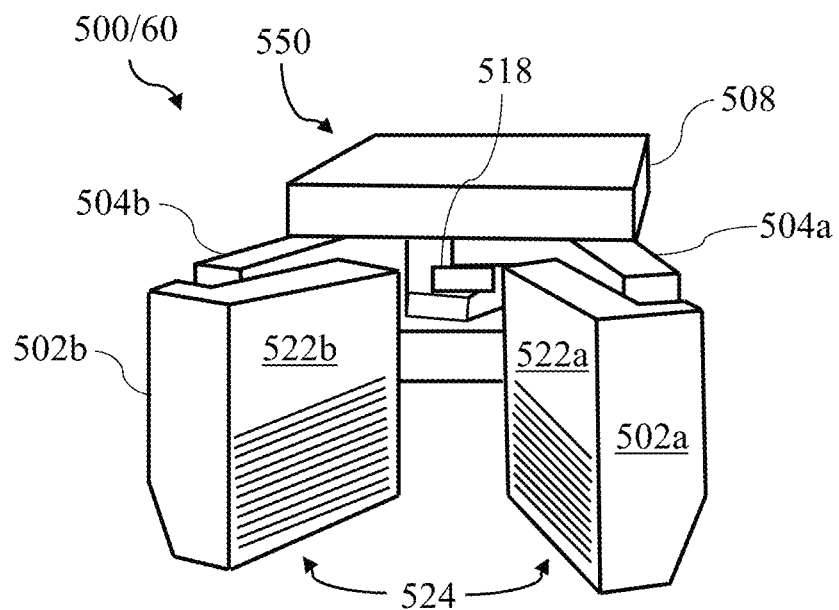
Figure 6:
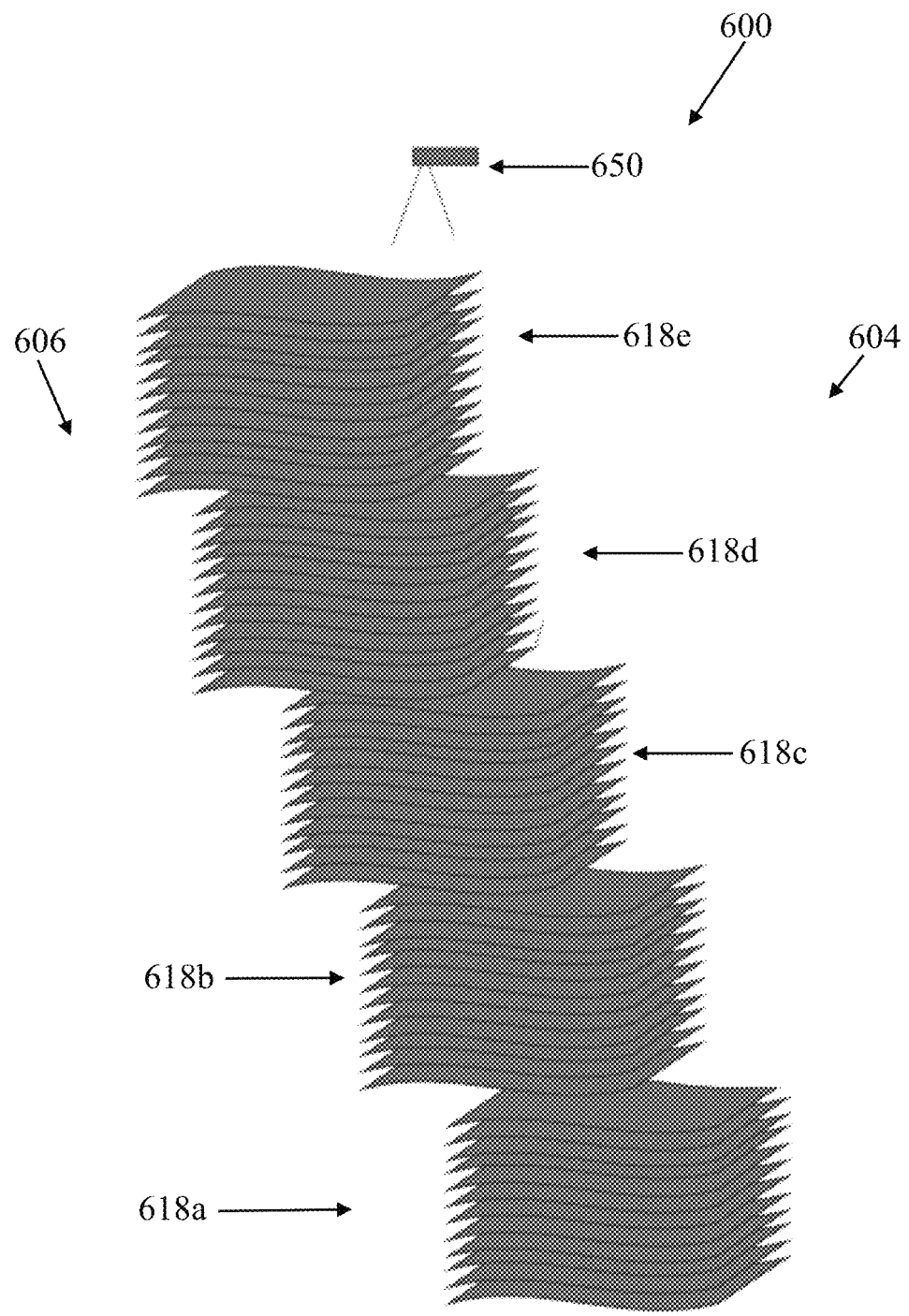
Figure 7A:
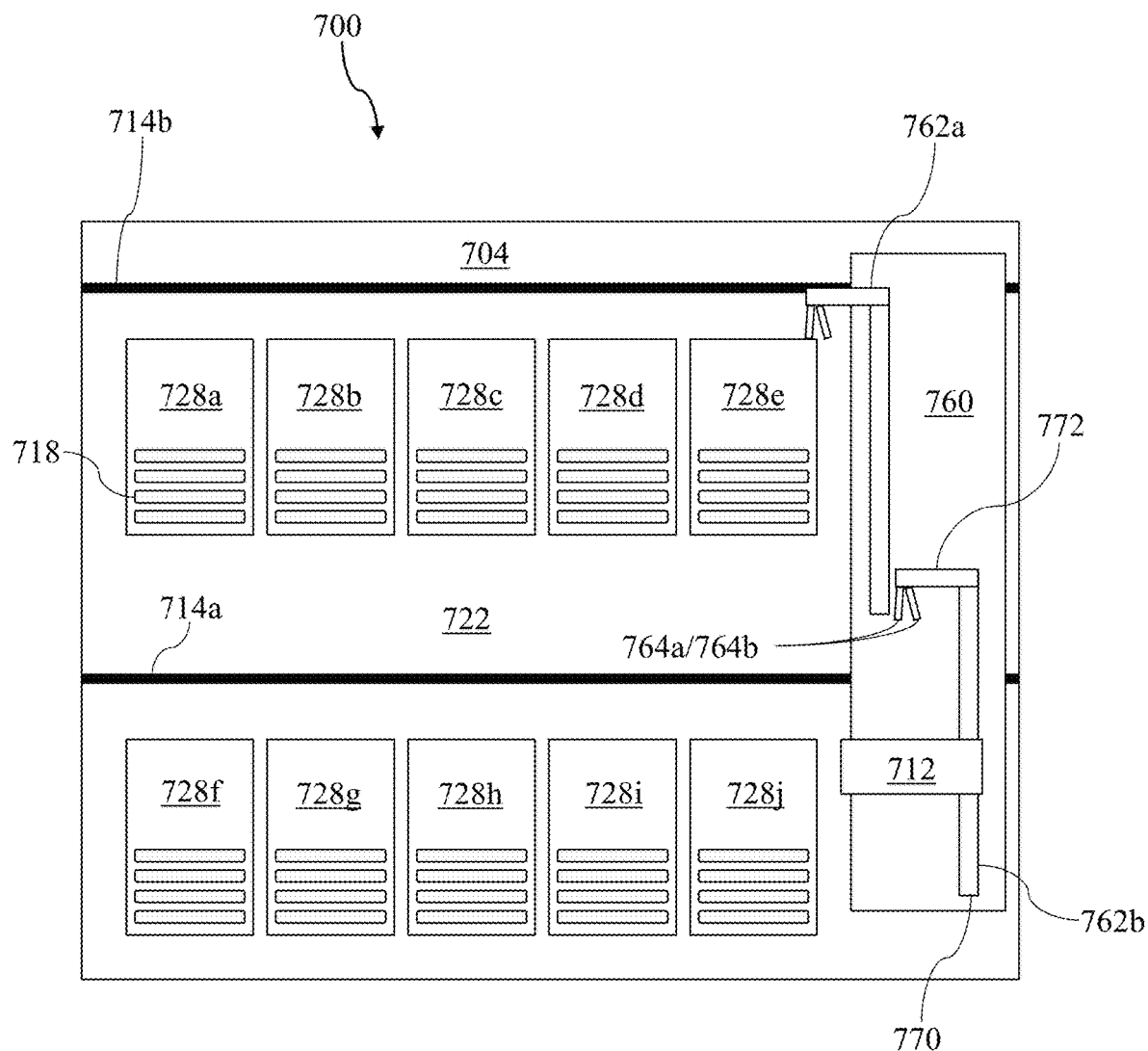
Figure 7B:
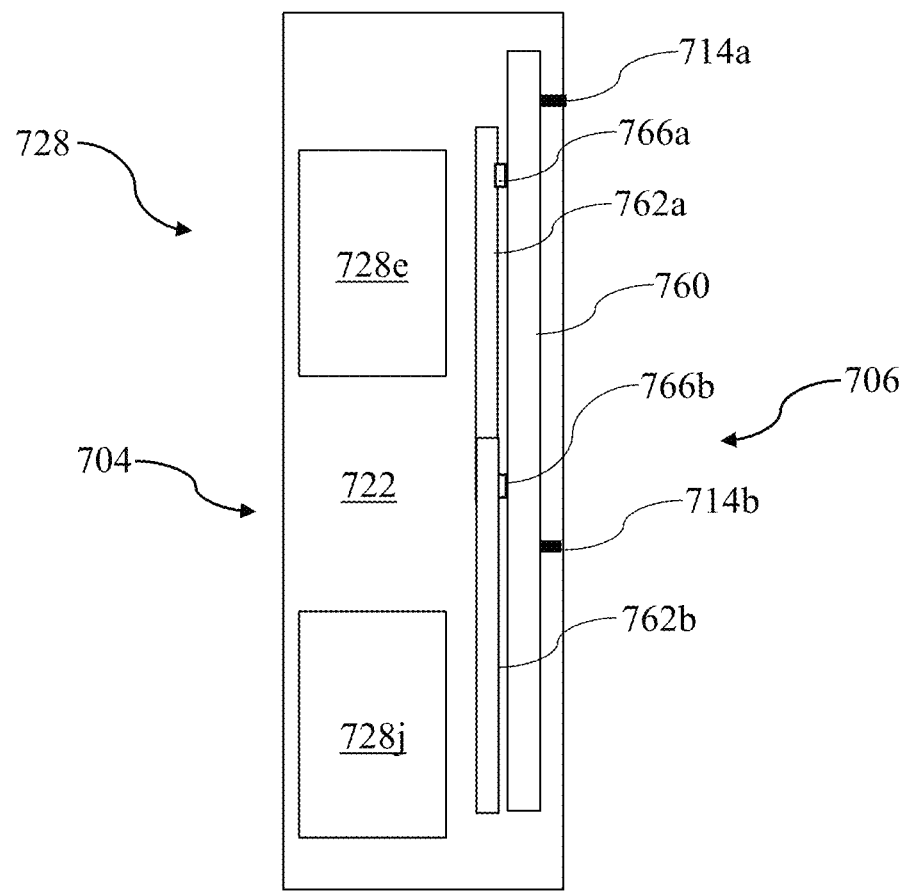
Figure 8A:
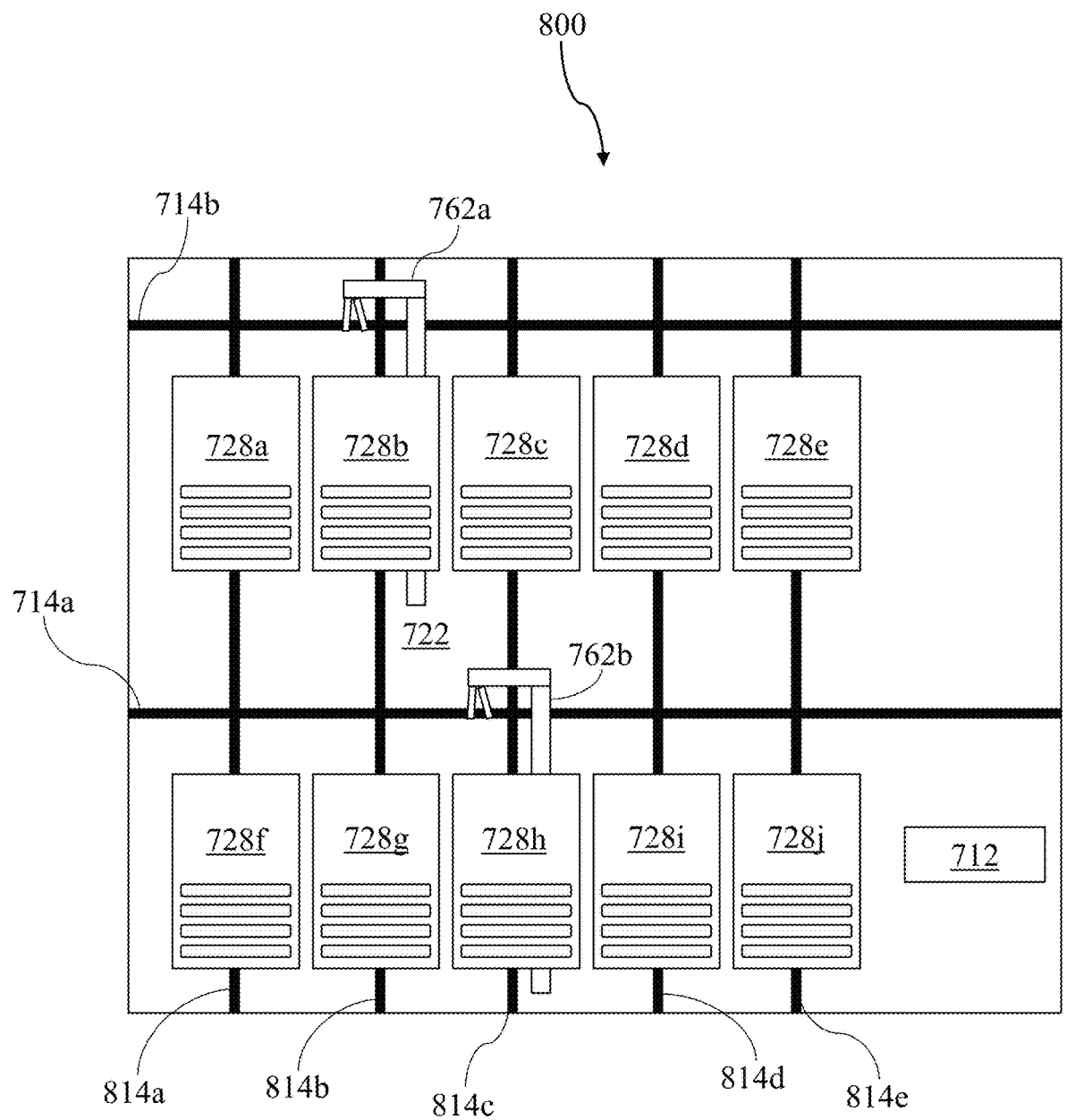
Figure 8B:
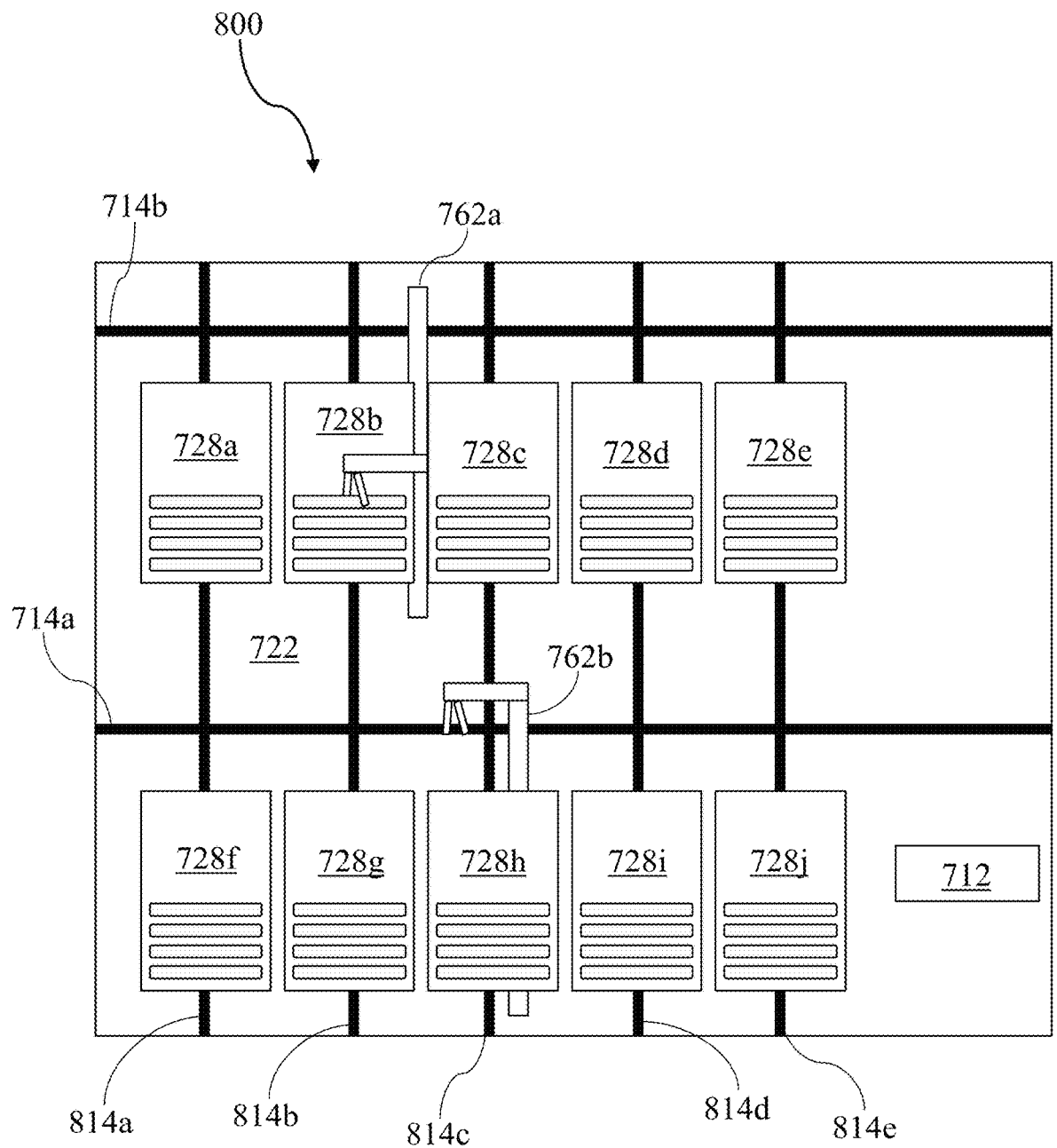
Figure 8C:
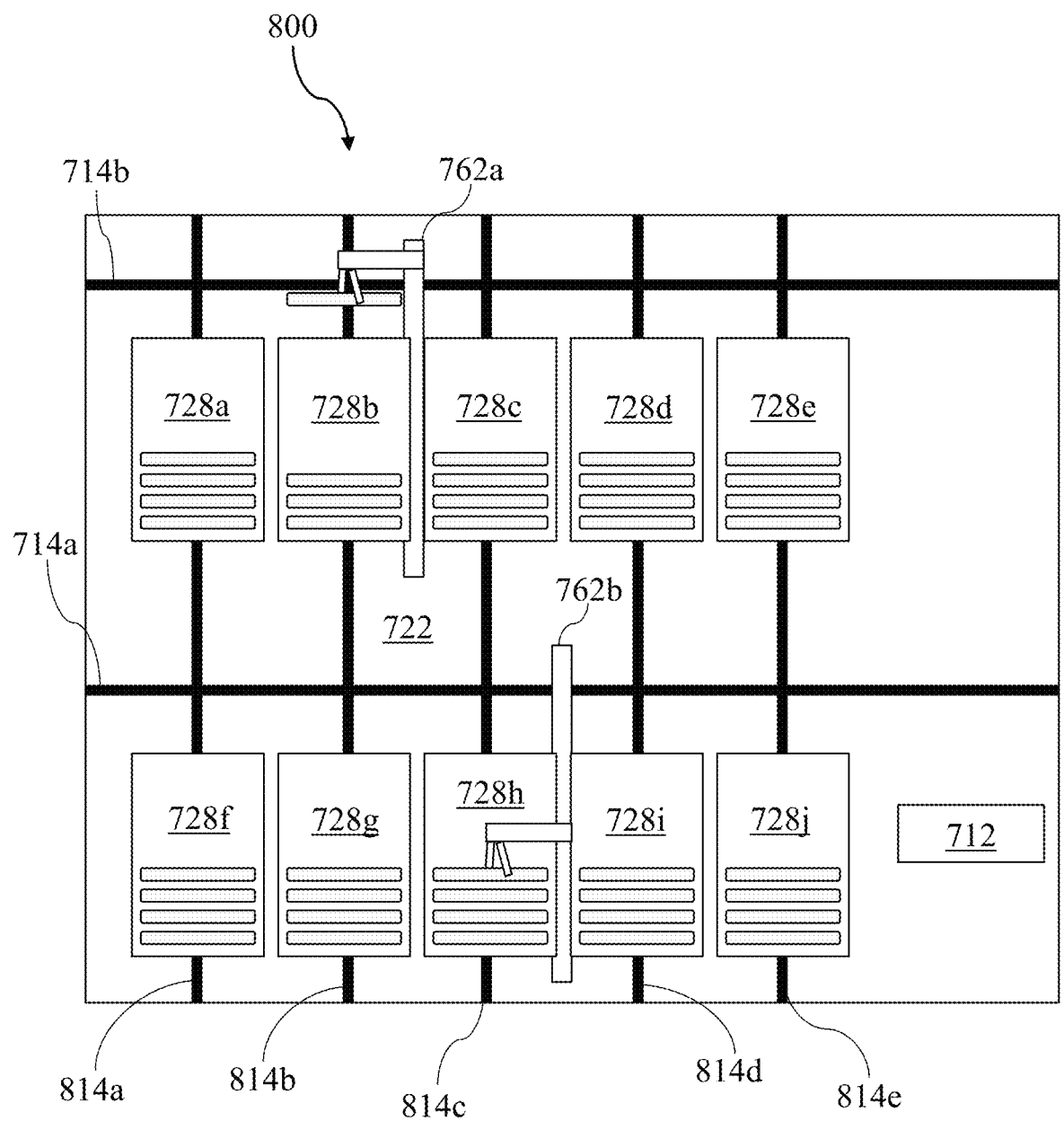
Figure 9:
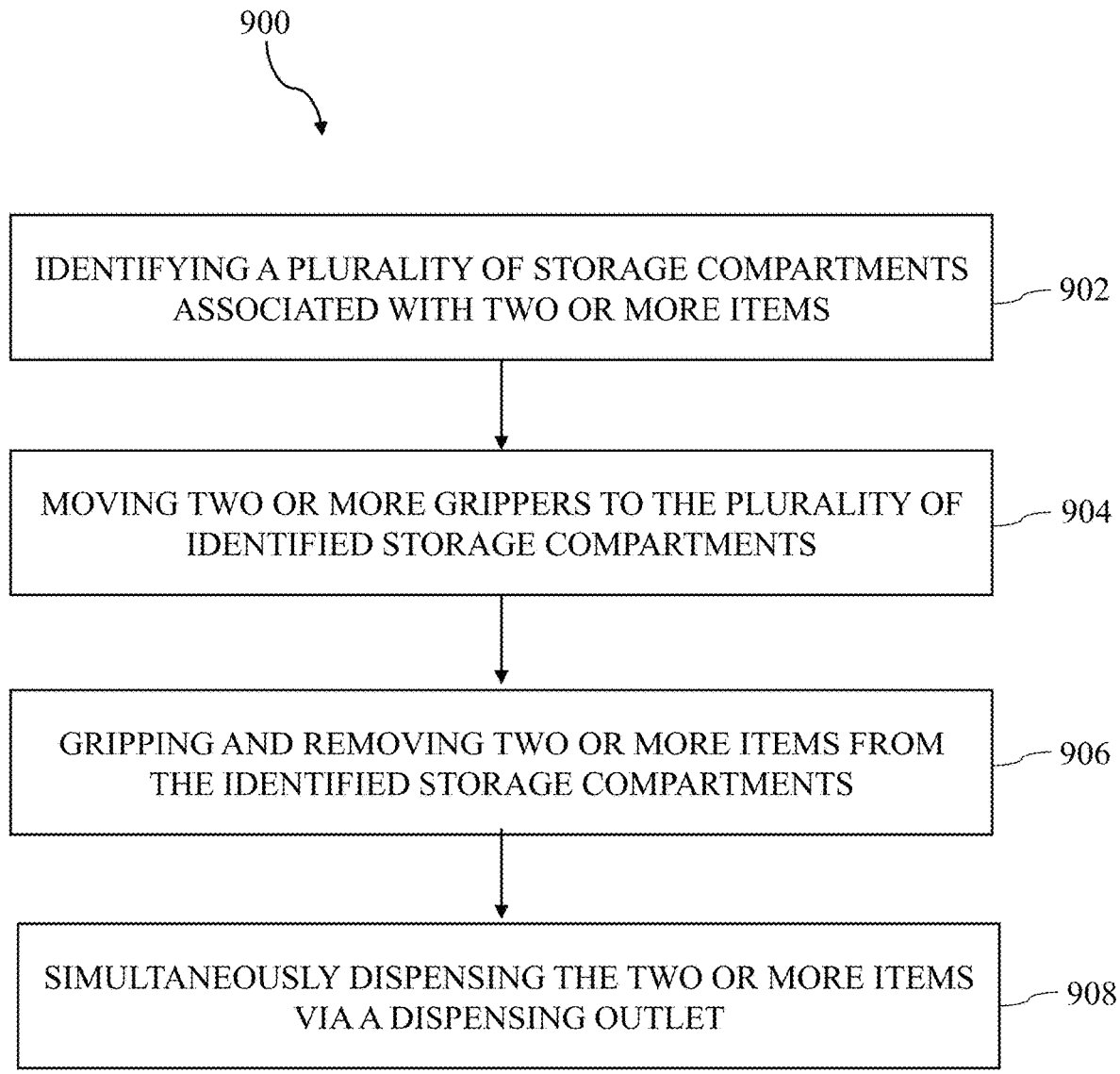
Figure 10A:
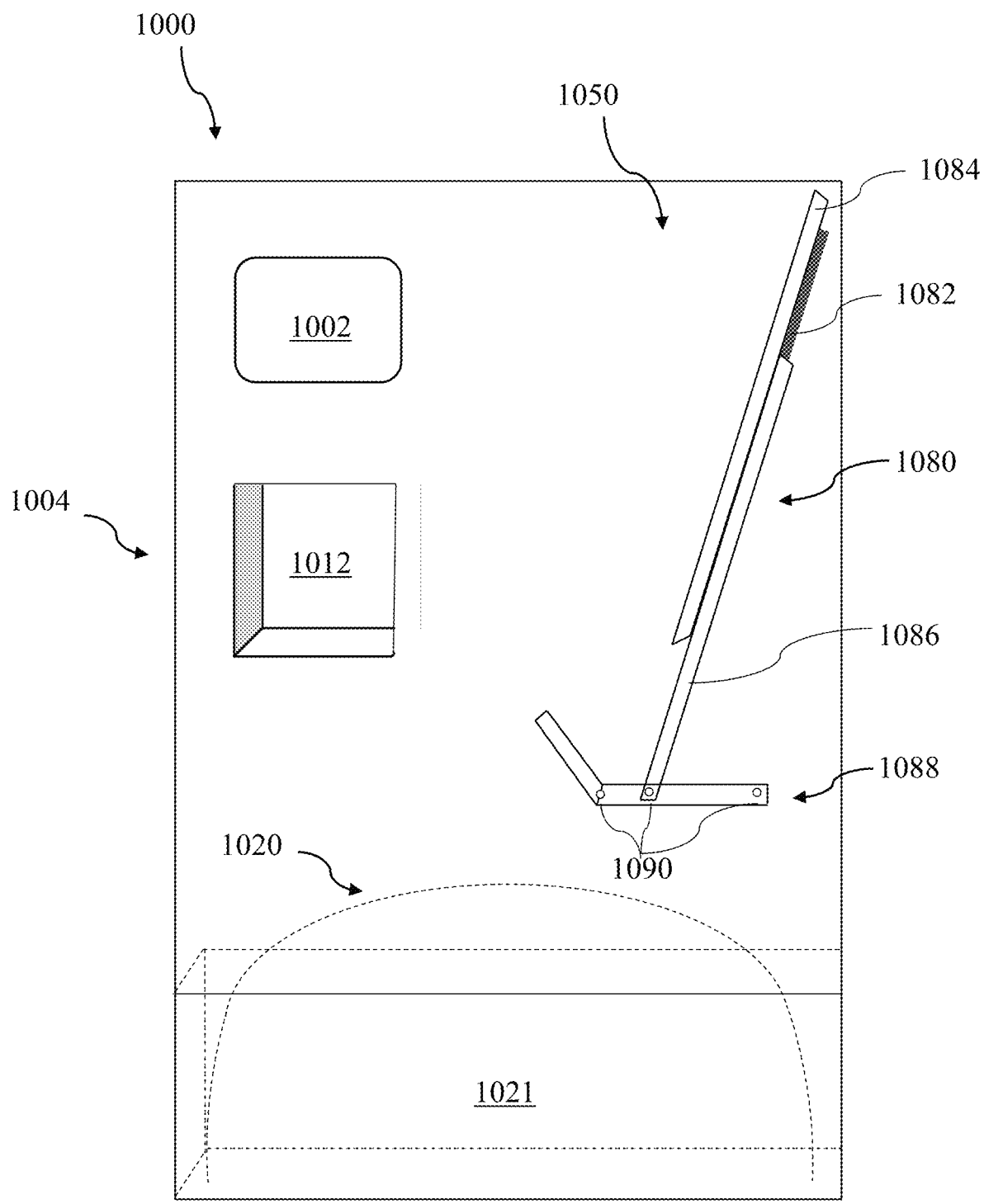
Figure 10B:
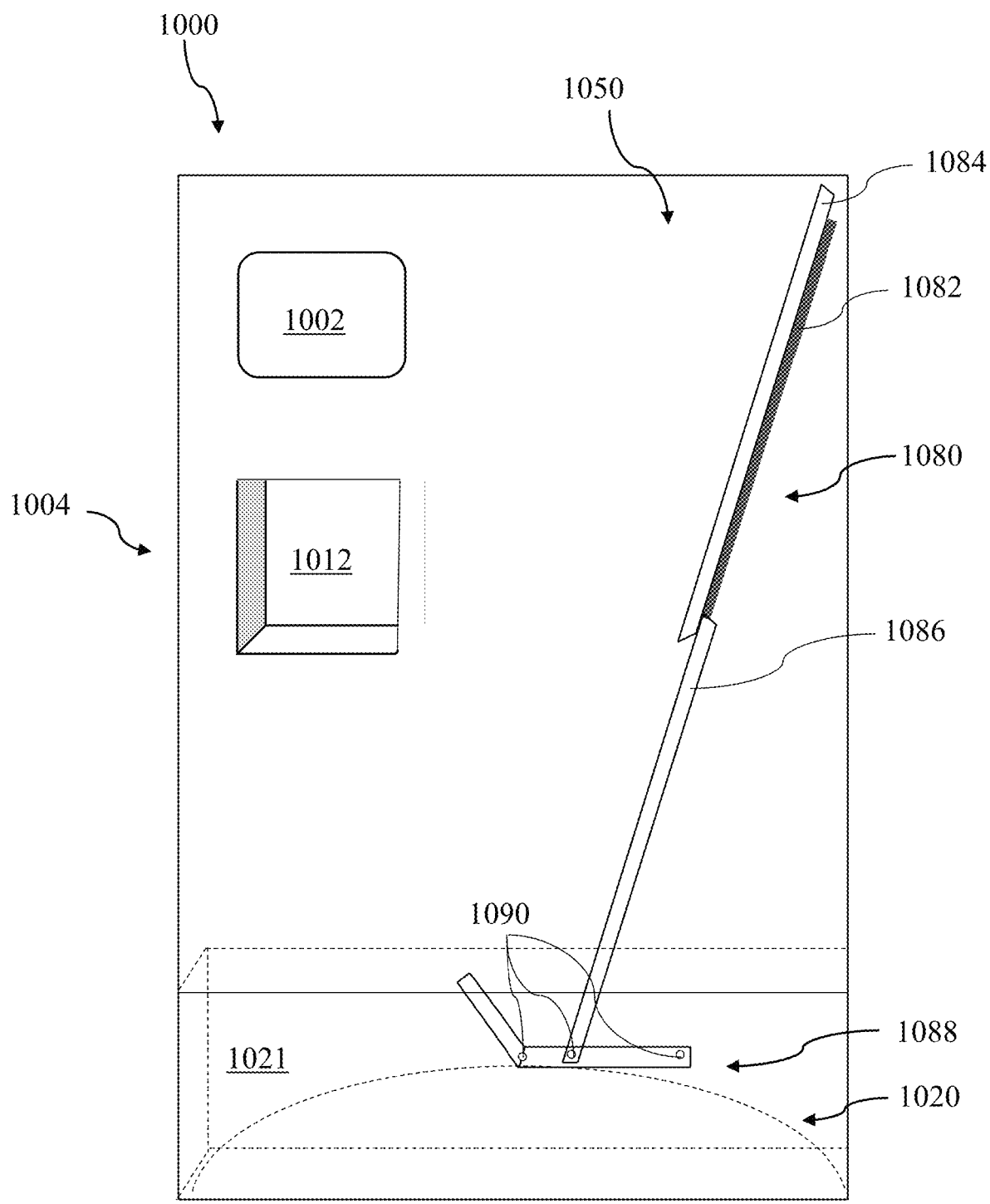

FIG. 1—a perspective front view of an automated dispensing system, according to some embodiments;

FIG. 2—a perspective front view of the internal space of the automated dispensing system of FIG. 1, having the front face thereof removed, according to some embodiments;

FIG. 3—a perspective view of a frontal cross section approximately at the center of the automated dispensing system of FIG. 1, according to some embodiments;

FIG. 4—perspective view of a frontal cross section in proximity to the back face of the automated dispensing system of FIG. 1, according to some embodiments;

FIG. 5A—a perspective enlarged view of a gripper assembly, according to some embodiments;

FIG. 5B and FIG. 5C—perspective enlarged views of a gripper assembly, according to some embodiments;

FIG. 6—a schematic drawing of a cross section side of arrangement of compartments/cells in a dispensing system, according to some embodiments;

FIG. 7A and FIG. 7B—a front view and a side view schematic illustrations of an item dispensing system, in accordance with some embodiments;

FIG. 8A, FIG. 8B, and FIG. 8C—front view schematic illustrations of an item dispensing system at three separate stages of operation during dispatchment of two items from two storage compartments of an item dispensing system, in accordance with some embodiments;

FIG. 9—a flowchart of functional steps in a method for simultaneously dispensing a plurality of items from an item dispensing system, in accordance with some embodiments;

FIG. 10A and FIG. 10B—front view schematic illustrations of a returning unit at two stages of operation during compression of returned items, in accordance with some embodiments.

DETAILED DESCRIPTION

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

According to some embodiments, there is provided an advantageous item dispensing system (also referred to as system) having one or more sets of movable shelves each having one or more compartments, the shelves are configured to move laterally towards and away a gripper assembly having an adjustable gripper, wherein the gripper assembly is configured to move along a horizontal and/or vertical axis, such that a coordinated/synchronized movement of the gripper assembly and the corresponding shelves allows a fast and accurate placement/positioning of the gripper assembly and a desired compartment holding or storing a selected item, to allow the adjustable gripper to adjustably grip the item and dispense the selected item to a user, via a dispensing outlet. In some embodiments, the gripper assembly is configured to move along/translate along plane defined by the horizontal and/or the vertical axis. In some embodiments, the gripper assembly may move diagonally (by coordinated or simultaneous movement along the horizontal and/or vertical axis thereof). In some embodiments, the gripper assembly may move behind the moving shelves). In some embodiments, after a suitable/corresponding item has been gripped by the gripper, the gripper is configured to move behind the shelves towards the dispensing outlet, in the most time-efficient manner (for example, in diagonal movement), to allow an enhanced item delivery time.

According to some embodiments, the item dispensing system is configured to dispense a plurality of items concurrently and/or simultaneously. According to some embodiments, the item dispensing system includes two or more gripper units configured to operate independently and/or individually from each other.

According to some embodiments, the item dispensing system includes a plurality of storage compartments configured for storage/holding of items. According to some embodiments, the storage compartments are arranged in rows and/or columns. According to some embodiments, the two or more gripper units are configured to move along at least one axis. According to some embodiments, each of the gripper units is configured to grip an item positioned within a designated storage compartment and deliver the gripped item to a dispensing outlet of the item dispensing system. According to some embodiments, the at least one axis and/or one of the at least two gripper units are configured such that the two or more gripper units are independently operable, thereby allowing simultaneous dispensing of two or more items, wherein each of the items originates from separate designated storage compartments.

In some embodiments, the item dispensing system includes one or more gripper assemblies that are each configured to move along a horizontal and/or vertical axis. In some embodiments, two or more gripper assemblies may have one or more common axes, such as, for example, a common X-axis and/or a common Y-axis. In some embodiments, two or more gripper assemblies have one or more separate axes, such as, for example, each having a separate X-axis and/or a separate Y-axis.

According to some embodiments, the item dispensing system is configured to dispense a plurality of items efficiently by dispensing two or more of the items simultaneously and/or concurrently. According to some embodiments, the item dispensing system includes two or more gripper units configured to operate independently, simultaneously, concurrently (semi-simultaneously), or at least partially consecutively, wherein each gripper unit is configured to pick up a different/separate item from a different storage compartment, simultaneously, or concurrently. According to some embodiments, the item dispensing system includes a processor coupled to one or more driving units configured to drive an operation of two or more gripper units individually. According to some embodiments, the operation of the two or more gripper units is independent of each other.

According to some embodiments, the concurrent dispensing of two or more items includes operation of two or more gripper units simultaneously. According to some embodiments, the concurrent dispensing of two or more items includes at least partially overlapping times of operation of the two or more gripper units.

According to some embodiments, an advantage of the item dispensing system including two or more gripper units configured to operate simultaneously and/or concurrently is in that the total time in which two or more items are dispensed is at least about 30%, 40%, 50%, 60%, 70%, 80%, 90% shorter than the total time in which two or more items are dispensed in an item dispensing system in which one or two gripper units are configured to operate consecutively. For example, an item dispensing system in which one or two gripper units are configured to operate fully consecutively may operate by dispensing a second item only after a first item has been dispensed.

According to some exemplary embodiments, the item dispensing system may be configured such that the total maximal user waiting time may be reduced, for example, from about 15.6 to about 9.8 seconds. According to some embodiments, the total maximal user waiting time includes the time between a user inputting data regarding requested items and the dispensing of all the requested items. According to some embodiments, the total maximal user waiting time includes the total operation time of the one or more gripper units. According to some embodiments, for example, the total dispensing time may be reduced from about 11.6 to about 5.8 seconds, per item, for a movement along the X axis, for example, for a dispensing of one item and two items, respectively. According to some embodiments, the item dispensing system is configured such that once two or more gripper units have each gripped an item, each of the gripper units release the gripped item consecutively or sequentially. According to some embodiments, the gripper units may be configured to release the items above a tray, channel, and/or shelf associated with a dispensing outlet of the item dispensing system. According to some embodiments, the item dispensing system includes an item exit sensor configured to identify an item during and/or after the gripper unit has released the item. According to some embodiments, the item dispensing system is configured such that a second item is only released once a first item is released and/or identified by the item exit sensor. In some embodiments, both items are accessible to a user essentially at the same time.

According to some embodiments, the item dispensing system may be configured such that the total maximal user waiting time may be reduced by implementing concurrent operation of two or more gripper units. According to some embodiments, the item dispensing system may be configured such that the total maximal user waiting time is reduced, for example, from about 8.4 seconds to about 4.2 seconds per item dispensed, in a movement along the X axis, for example, for a dispensing of one item and two item, respectively, by implementing concurrent operation of two or more gripper units. According to some embodiments, the item dispensing system may be configured such that the total maximal user waiting time is reduced by at least about 2 to about 8 seconds, by implementing concurrent operation of two or more gripper units. According to some embodiments, the item dispensing system is configured such that the total maximal user waiting time may be reduced by about 2 to about 6 seconds per additional item (any item after the first dispensed item). According to some embodiments, the item dispensing system may be configured such that the total maximal user waiting time is reduced from about 9.8 seconds to about 7.8 seconds for the dispensing time of at least two items.

According to some embodiments, the two or more gripper units operating concurrently may include any type of movement and/or adjustment of the two or more gripper units at the same time. According to some embodiments, and as described in greater detail below herein, the two or more gripper units may be adjusted simultaneously while executing different operational commands. For example, one of the gripper units may adjust a position of one or more probes configured to grip an item from one of the storage compartments while a second gripper unit may move along a horizontal axis towards a second storage compartment containing a second item.

According to some embodiments of the present invention there is provided a method for concurrently dispensing a plurality of items from an item dispensing system, including identifying a plurality of storage compartments associated with two or more items, moving/placing two or more gripper units (each associated with a corresponding gripping assembly, or sharing a common gripping assembly) to the plurality of identified storage compartments, removing one or more items from the identified storage compartments, and dispensing the items, using the two or more gripper units and/or gripping assemblies, through a dispensing outlet, wherein the dispensing is performed in a concurrent manner, i.e., the plurality of gripped items are dispensed in the same time. According to some embodiments, the method includes operating the two or more gripper units (and/or the gripping assemblies) in synchronization, simultaneously or at least semi-simultaneously (for example, consecutively). According to some embodiments, the method includes dispensing the plurality of items simultaneously and/or concurrently.

In some embodiments, the items dispensed may include any type of item, such as, for example, flexible products, newspapers, textile items, including any type of clothing, such as, garments, pants, shirts, scrubs, lab coats, aprons, and the like, or any combination thereof. In some embodiments, the items are textile items, such as, for example, but not limited to: garments, pants, shirts, scrubs, gowns, robes, towels, and the like, or any combination thereof. Each possibility is a separate embodiment.

In some embodiments, there is provided an advantageous item dispensing system having a plurality of grippers. In some embodiments, the item dispending system includes at least one, at least two, at least three, or at least four grippers. Each possibility is a separate embodiment. In some embodiments, at least one of the plurality of grippers is adjustable. In some embodiments, the plurality of grippers are adjustable. In some embodiments, one or more gripper assemblies include a plurality of grippers. In some embodiments, one or more gripper assemblies include at least two, at least three, or at least four grippers. Each possibility is a separate embodiment.

According to some embodiments, the item dispensing systems disclosed herein may include at least two gripper units, each may operate independently, to allow the gripping of at least two separate items (set of items), and the concurrent dispensing of the items to a user, resulting in improved overall dispensing time. According to some embodiments, the item dispensing system may include two or more shelves that are concurrently moveable. According to some embodiments, the concurrent dispensing of two or more items includes operation of two or more gripper units simultaneously or concurrently. According to some embodiments, the concurrent dispensing of two or more items includes at least partially overlapping times of operation of the two or more gripper units.

Reference is now made to FIG. 1, which shows a perspective front view of an automated item dispensing system 100, according to some embodiments. As shown in FIG. 1, item dispensing system 100 is in the form of a container having at least a front face 104 and a back face 106. The external side of the front face has one or more doors (as a non-limiting example, shown as doors 108*a* and 108*b*), that are configured to be opened, for example, sideways. The opening of the doors allows reaching the internal volume of the dispensing system, to allow loading items, perform maintenance routines, etc. In some embodiments, the system may include one or more doors along one or two sides of the system, e.g., a wall positioned normal to the back face 106 and/or the front face 104.

According to some embodiments, doors 108*a* and/or 108*b* may include one or more display windows (not shown). According to some embodiments, the one or more windows may include a transparent and/or semi-transparent wall. According to some embodiments, the one or more display windows are flush with one or more portions of the doors 108*a* and/or 108*b*.

As further detailed below, the internal volume of the system includes one or more compartments/cells, configured to hold/store various items to be dispensed. The compartments may be arranged in any desired arrangement, such as, for example, in sets in shelves, in rows and/or columns. The compartments may be similar or different as to size, shape, volume, capacity, and the like. Each of the compartments may be capable of including/storing/holding one or more articles that may be stored in any desired orientation, such as, for example, in vertical stacks. In some embodiments, the items may be of any type, such as, for example, flexible products, textile, towels, newspapers, clothing, including, garments, pants, shirts, scrubs, aprons, lab coats, doctor coats, and the like, or any combination thereof. In some embodiments, the items (such as, for example, cloths) may be folded or un-folded and may be stored as is, or in a suitable bag or cover. In some embodiments, the items stored in each compartment may be similar, identical or different with respect of quantity (such as number) and/or quality (such as, type, size, color, condition of the item, defects in the item, packaging of the items, and the like, or any combination thereof).

As further shown in FIG. 1, item dispensing system 100 further includes a user interface 102, which allows a user to interact with the system, for example, by indicating a desired item to be retrieved. According to some embodiments, user interface 102 is positioned along an outer portion of the item dispensing system 100, such as, for example, one or more portions of the doors 108*a* and/or 108*b*.

The user interface may include any type of user interface, including, for example, but not limited to: keyboard, monitor, screen, display, touch-screen, vocal activated interface, face recognition interface, use of QR code, smartphone application, and the like. According to some embodiments, user interface 102 is coupled to a processor (not shown). According to some embodiments, user interface 102 is configured to receive input from a user and/or display output to a user from the processor. According to some embodiments, the processor is configured to communicate with the user interface 102, thereby being configured to control the operation of a gripping assembly located within the internal space of the system in accordance with a user command. According to some embodiments, the processor includes a memory module. According to some embodiments, the processor and/or the memory module includes an algorithm configured to operate the item dispensing system 100. According to some embodiments, the processor is in communication with any other systems and/or any other external units, via any suitable wired or wireless route. For example, in some embodiments, the processor is in communication with one or more control units configured to control and regulate the operation of a gripping assembly located within the internal space of item dispensing system 100. According to some embodiments, the processor is in communication with the one or more driving units. According to some embodiments, the processor is configured to control the operation of the one or more driving units.

According to some embodiments, the user interface can interact with an internal controller (not shown), which is configured to control the operation of a gripping assembly located within the internal space of the system.

As further detailed below, the gripping assembly includes a gripping unit having an adjustable gripper, having one or more movable arms configured adjustable hold/grip an item, to allow retrieving (picking up and dispensing) the selected item(s) from a corresponding compartment. The gripping assembly may further optionally include one or more motors, arms, moving platform(s), and the like, as further detailed below. The gripping assembly may further optionally include one or more adjustable grippers. The gripping assembly may further optionally include a plurality of adjustable grippers. According to some embodiments, the gripping assembly may further optionally include one or more sensors, configured to enable the identification of the specified items, the position of the item, the distance from the item, or any combination thereof. According to some embodiments, the sensors may include a proximity or distance sensors (such as a laser sensor), an RFID reader, a friction sensor, a weight sensor, a light sensor, and the like, or any combination thereof.

As shown in FIG. 1, front face of system 100 further includes an opening (also referred to as dispensing outlet) 112, through which an item that has been retrieved from its storage location in a compartment is being dispensed from the system, for example via a suitable chute, through dispensing outlet 112, to be accessible a user. In some embodiments, the system may further include an optional communication unit, configured to allow communication of the system with any other systems and/or any other external units, via any suitable wired or wireless route. In some embodiments, the system may include, or be associated with a returning unit. According to some embodiments, the back face 106 of item dispensing system 100 may optionally include one or more doors, configured to be opened by a user to allow reaching the internal space of the system, for example, to allow loading the compartments with items, for maintenance purposes, and the like. In some embodiments, one or more of the shelve(s) may be configured to be at least partially pulled out (be removed/released) from the container (via the respective opened doors) to allow loading the compartments with items. In some embodiments, the system further includes an item management assembly (not shown) and optional communication unit (that may be a separate unit or be part of the controller/processor unit of the system). In some embodiments, item dispensing system 100 may be in the form of a cabinet or cupboard.

According to some embodiments, item dispensing system 100 may include a disinfecting and/or cleaning unit. According to some embodiments, the disinfecting and/or cleaning unit is positioned approximate to one or more of the dispensing outlet 112 and/or the returning unit. According to some embodiments, dispensed items and/or returned items are disinfected and/or cleaned by the disinfecting and/or cleaning unit.

According to some embodiments, the dispensing outlet 112 may include a channel configured to fit two or more items simultaneously. According to some embodiments, the dispensing outlet 112 is configured to receive one or more items form gripper units and/or gripping assemblies, as further elaborated. According to some embodiments. the dispensing outlet 112 (or a portion of the dispensing outlet 112) may be extending through the front face 104 for user accessibility.

Reference is now made to FIG. 2, which shows a perspective front view of internal space of the dispensing system, having the front face removed, according to some embodiments. Shown in FIG. 2 is item dispensing system 100, in which the front face (i.e., doors and panels, such as but not limited to front face 104 shown in FIG. 1) has been removed to reveal the internal space of the system. As detailed above, item dispensing system 100 has a front side 104 and a back side 106. The front face/side is facing a user and is the side from which the items are dispensed from a suitable dispensing unit which includes a dispensing outlet and a dispensing chute 126. The internal volume/space 122 of item dispensing system 100 includes a plurality of compartments/cells (represented as compartments 128a-f), which may be arranged in columns and rows/tiers. The compartments 128a-f shown in FIG. 2 are arranged in rows/shelves, such as shelf 130a. It is to be understood that any number of shelves/rows/columns may be accommodated within the internal volume of the system, and for simplicity only one such shelves having 6 compartments is illustrated in FIG. 2, whereas additional shelves or columns are omitted. The various cells/compartments may be similar or different with respect of size, shape, volume, capacity, and the like. Each of the compartments/cells may be capable of including/storing/holding one or more articles/items that may be stored in any desired orientation, such as, for example, in vertical stacks. The items may be any type of items, such as, for example, any type of clothing, including, garments, pants, shirts, scrubs, apron, lab coat, doctor coat, and the like, or any combination thereof. In some embodiments, the garments may be folded or un-folded and may be stored as is, or in a suitable bag or cover. In some embodiments, the items stored in each compartment may be similar, identical or different with respect of quantity and/or quality. In some embodiments, the items stored in each row or column may be similar, identical or different with respect of quantity. The various compartments/cells are configured to move laterally between the front face (side) and the back side (face) of the system, in the direction of a Z-Axis. Depending on the setting of the system, each of the compartments or some of the compartments may move individually in the lateral direction, or each group of compartments (for example, compartments arranged in a row or in a column) may move laterally. In the example shown in FIG. 2, shelf 130a including compartments 128a-f may move laterally between the front side and the back side of the system. The movement of the compartments/shelves is actuated by suitable actuating unit which includes combination of motors, arms, pistons, rails, shafts, cables, screws and/or pullies, to allow the coordinated movement of the compartments/shelves along the Z-Axis. Each of the compartments or each of the shelves may have an independent corresponding actuating unit. In some embodiments, common elements of the actuating unit (such as, a motor) may be shared between individual actuating units. In one embodiment, the lateral movement may be actuated, at least partially using one or more pistons, such as, piston 136a, which may be placed on a support rail. In a starting/resting position, the shelves are located in close proximity to the front face of the system. When dispensing an item is initiated, the compartment or the shelf with the corresponding compartment holding the item may move laterally towards the back face of the system, where the gripping assembly is situated. In some exemplary embodiments, the lowest shelf may be stationary and one or more upper shelves maybe movable. In some embodiments, the lowest shelf is placed such that it is located closer to the back face of the container. The gripping assembly is configured to move at least along a vertical axis (X-axis) and a horizontal axis (Y-axis) along or in close proximity to the back wall. The movement of the gripper assembly is actuated using a gripper assembly actuating unit, which includes a combination of motors, arms, pistons, rails, shafts, cables, screws and/or pullies, to allow the coordinated movement of the gripper assembly at least along the X-Axis and the Y-axis. The gripper assembly is not shown in FIG. 2, however, exemplary portions of the gripper assembly actuating unit are illustrated, including, motor 140 and chains 142a-b, which allows the horizontal and vertical movement of the gripper assembly, as further detailed, below. Further shown in FIG. 2 is top drawer cover 144, which allows user accessibility for performing maintenance as well as positioning one or more sterilization units, as detailed below.

Reference is now made to FIG. 3, which shows a perspective view of a frontal cross section approximately at the center of the automated dispensing system of FIG. 1, according to some embodiments. As shown in FIG. 3, item dispensing system 100, which is in the form of a container has a front side (face) 104 and a back side (face) 106. The front face is facing a user and is the side from which the items is dispensed (via dispensing unit, as detailed below). The internal volume/space 122 of item dispensing system 100 includes a plurality of compartments/cells (such as but limited to compartments 128a-f), which may be arranged in columns and rows/tiers. Compartments/cells 128a-f shown in FIG. 3 are arranged in rows/shelves, such as shelf 130a. It is to be understood that any number of shelves/rows/columns may be accommodated within the internal volume of the system, and for simplicity only one such shelves having 6 compartments is illustrated in FIG. 3, white additional similar (or different) shelves or columns are omitted. The various cells/compartments may be similar or different with respect of size, shape, volume, capacity, and the like. The various compartments are configured to move laterally between the front face (side) and the back side (face) of the system, in the direction of a Z-Axis. In some embodiments, some of the compartments and/or shelves are movable and some may be stationary. In some embodiments, at least some of the compartments/shelves are movable and at least one (for example, the lowest one) is stationary. Depending on the setting of the system, each of the compartments may move individually in the lateral direction, or each group of compartments (for example, compartments arranged in a row or in a column) may move laterally. In the example shown in FIG. 3, shelf 130a including compartments 128a-f may move laterally between the front side and the back side of the system. The movement of the compartments/shelves is actuated by suitable actuating unit which includes combination of motors, arms, pistons, rails, shafts, cables, screws and/or pullies, to allow the coordinated movement of the compartments/shelves along the Z-Axis. Each of the compartments or each of the shelves may have an independent corresponding actuating unit. In some embodiments, common elements of the actuating unit (such as, a motor) may be shared between individual actuating units. In one embodiment, the lateral movement may be actuated, at least partially using one or more pistons, such as, piston 136a, which may be placed on a support rail. In a starting/resting position, the shelves are located in close proximity to the front face of the system. When dispensing an item is initiated, the compartment or the shelf with the corresponding compartment holding the item may move laterally towards the back face of the system, where the gripping assembly is situated. In some embodiments, the lateral movement of the compartments/shelves may be adjustable, based on the type of items in the cell (for example, large items—move closer to the back). According to some embodiments the compartments width and/or height may be adjustable to allow accommodation of different types of items. In some embodiments, the gripping assembly is configured to move at least along a vertical axis (X-axis) and a horizontal axis (Y-axis) along or in close proximity to the back wall. The movement of the gripper assembly is actuated using a gripper assembly actuating unit, which includes a combination of motors, arms, pistons, rails, shafts, cables, screws and/or pullies, to allow the coordinated movement of the gripper assembly at least along the X-Axis and the Y-axis. The gripper assembly is not shown in FIG. 3, however, exemplary portions of the gripper assembly actuating unit are illustrated, including, motor 140 and chains 142a-b, which allows the horizontal and vertical movement of the gripper assembly, as further detailed, below. Further shown in FIG. 3 is top drawer 146, which allows user accessibility for performing maintenance as well as positioning one or more sterilization units, as detailed below.

Reference is now made to FIG. 4, which shows a perspective view of a frontal cross section in proximity to the back face of the automated item dispensing system 100 of FIG. 1, according to some embodiments. The cross section shown in FIG. 4 shows the back side 106a of the item dispensing system. As detailed above, the back side may be stationary fixed wall, or in some embodiments, may include one or more doors/openings allowing reaching the internal space of the item dispensing system from the back side, for either technical maintenance purposes and/or for loading items with corresponding compartments. The compartments/shelves illustrated in FIGS. 2-3 are omitted from the cross section of FIG. 4. As shown in FIG. 4, in close proximity to the back side 106a, gripper assembly 150 is situated. Gripper assembly 150 is configured to move at least horizontally and vertically, along the X and Y-Axes. The movement of the gripper assembly is actuated/controlled by a corresponding gripper assembly actuating unit which may include any suitable combination of one or more of: motors, arms, platforms, rails, chains, pullies, pistons, belts, screws, shafts, and the like, to allow the smooth, accurate and fast movement of the gripper assembly at least along these axes. Shown in FIG. 4 are exemplary elements of the gripper assembly actuating unit, including, motor 140, chains 142a-b, cables 144 and a movable arm 148, are arranged in rows/shelves, such as shelf 130a. It is to be understood that any combination of actuating elements may be used. Thus, when an item is selected for dispensing, lateral movement of the corresponding compartment holding the item (or the shelf holding the compartment) from the front face of the item dispensing system towards the back face of the item dispensing system, wherein the gripper assembly is positioned, is initiated. In addition, horizontal and/or vertical movement of the gripper assembly (actuated by the corresponding actuating unit) is initiated before, after or concomitantly with the vertical movement of the compartment/shelves. By the coordinated movement of the compartment/shelves and the gripper assembly, the adjustable gripper unit of the gripper assembly is positioned in the compartment from which the item is to be picked. Once the gripper unit is correctly positioned, the adjustable gripper/gripping unit can adjustably grip the item, pick it up and carry/direct the item (under the control of the actuating unit) to the dispensing unit, whereby, the item can be dispensed, via the dispensing chute to be accessible to a user via the dispensing outlet located in the front face of the system. By such setting of coordinated lateral movement of the compartments/ shelves and the vertical-horizontal movement of the gripper assembly, a fast and accurate positioning of the gripper unit in the correct compartment is achieved, which is followed by the adjustable gripping of the item in the most accurate and efficient manner, to allow the dispensing thereof. In some embodiments, the adjustable gripping may include, for example, adjustable gripping tense/force, adjustable gripping position of the item, and the like. In some embodiments, the adjustable gripping is predetermined or customizable. For example, adjustable gripping tense maybe determined based on the type of item (pants versus shoes), condition of item (folded vs. non-folded, wrapped vs. unwrapped, etc.), number of items in a compartment, and the like, or any combination thereof. According to some embodiments, by utilizing such settings, time and space saving advantageous item dispensing systems, which provide an accurate dispensing, are obtained. In further embodiments, the adjustable gripping further allows an item to be dispensed in a proper manner (for example, folded manner, rather than curled or otherwise compromised), even if the item is not wrapped or stored in a bag.

Reference is now made to FIG. 5A, which shows a perspective enlarged view of a gripper assembly 160, according to some embodiments. As shown in FIG. 5A, gripper assembly 160 includes one or more arms/rails, shown as exemplary rails 170a-e, configured to attach/ function with a corresponding actuating unit and/or to hold and adjust the position of adjustable gripping unit 162. The rails may be functionally and/or physically connected to each other. The rails may be connected permanently or via connecting elements such as, hinges, allowing at least some degree of movement between one or more rails. For example, rails 170e, connecting the adjustable gripping unit 162, is connected by hinges to rails 170A and to the gripping unit, to thereby allows at least one degree of freedom to the adjustable gripping unit. Adjustable gripping unit 162 includes two movable arms 164a-b, configured to open and close, to allow gripping an item between the arms. At least one of the arms may include spikes to improve gripping of an item. In some embodiments, an adjustable spring allows the translational movement of the gripping arms, to allow adjusting the gripping force. In some embodiments, the arms may include one or more sensors, configured to allow in aiding identifying the item, the position of the item, the distance from the item, the and the like. In some embodiments, the sensors may include a proximity or distance sensors (such as a laser sensor), an RF ID reader, a friction sensor, a weight sensor, a light sensor, and the like, or any combination thereof. Each possibility is a separate embodiment. According to some embodiments, the gripper assembly allows movement of the adjustable gripper unit along the X-Axis and/or along the Y-Axis, to allow the gripper to reach any desired spatial location. The gripper assembly may include one or more means for moving the one or more gripper units, such as, one or more suitable motors, one or more moving platforms/arms/tracks rails, one or more controllers, and the like, which ultimately allow the control of the movement of the gripper unit to direct the gripper to a specific location. In some embodiments, the gripper unit is situated on a moving rail. In some embodiments, the gripper assembly may include horizontal and/or vertical arms or tracks, along which the gripper unit can move, for example, by a motor driven belt or any other suitable means. In some embodiments, the adjustable gripper unit is advantageous as it allows gripping various types of items, at various conditions in the most accurate, sensitive and fast manner, thereby allowing successfully dispensing a wide variety of items.

Reference is now made to FIG. 5B and FIG. 5C, which are perspective enlarged views of a gripper assembly, according to some embodiments. According to some embodiments, the gripper assembly 500/60 and/or the gripper unit may include two or more arms 502a/502b. According to some embodiments, the two or more arms 502a/502b may extend from a gripper body 508 of the gripper assembly 500/60 and/or the gripper unit. According to some embodiments, the gripper assembly 500/60 and/or the gripper unit may be adjustable. According to some embodiments, the two or more arms 502a/502b may be adjustable in relation to each other and/or in relation to the gripper body 508. According to some embodiments, each of the two or more arms 502a/502b may have at least three, at least four, at least five, or at least six degrees of freedom.

According to some embodiments, the two or more arms 502a/502b may include plates each having an inner surface 522a/522b which may be positioned to face each other at a closed configuration of the gripper assembly 500/60 and/or the gripper unit. According to some embodiments, one or more of the inner surfaces 522a/52b may include one or more of a ridged surface, an uneven surface, a sticky surface, or the like. According to some embodiments, such as depicted in FIG. 5C, at least a portion of the inner surfaces 522a/52b may include ridged surface 524.

According to some embodiments, the two or more arms 502a/502b may be coupled to the gripper body 508 via one or more probes 504a/504b. According to some embodiments, the one or more probes 504a/504b may be slidable in relation to the gripper body 508. According to some embodiments, the one or more probes 504a/504b may be coupled to one or more of the arms 502a/502b at a first end thereof and coupled to the gripper body 508 at a second end thereof. According to some embodiments, the one or more probes 504a/504b may be configured to translate the one or more arms 502a/502b in relation to the gripper body 508. According to some embodiments, the one or more probes 504a/504b may be coupled to the gripper body 508 via one or more hinges 518. According to some embodiments, the one or more probes 504a/504b may be slidable in relation to the gripper body 508 via one or more rail 510 and/or one or more sliding hinge 506. According to some embodiments, the gripper body 508 may include a cavity configured to contain at least a portion of the one or more probes 504a/504b at a closed configuration thereof. According to some embodiments, the gripper body 508 may be coupled to an extender 516 configured to couple to one or more rails of the dispensing system. According to some embodiments, the extender 516 may be coupled to the gripper body 508 via one or more of a rigid connector 512 and/or a hinge 514.

Reference is now made to FIG. 6, which is a schematic drawing of a cross section side view of arrangement of compartments/cells of an item dispensing system, according to some embodiments. In item dispensing system 600 shown in FIG. 6, items are arranged in a plurality of compartments, shown as compartments 618a-d. The compartments may be arranged in rows and/or columns and may hold any type of items. The various cells/compartments may be similar or different with respect of size, shape, volume, capacity, and the like. Each of the compartments may be capable of including/storing/holding one or more articles/items that may be stored in any desired orientation, such as, for example, in vertical stacks. The items may be any type of items, such as, for example, any type of clothing, including, garments, pants, shirts, scrubs, apron, lab coat, doctor coat, and the like, or any combination thereof. In some embodiments, the garments may be folded or un-folded and may be stored as is, or in a suitable bag or cover. In some embodiments, the items stored in each compartment may be similar, identical or different with respect of quantity and/or quality. In some embodiments, the items stored in each row or column may be similar, identical or different with respect of quantity. As shown in FIG. 6, the compartments are positioned/arranged such that they are located at different distances from the front face (604) or back face (606) of the item dispensing system 600. The system further includes a gripper assembly 650 (having a gripper unit having at least two movable arms), that can move along horizontal and vertical axes. By such arrangement of compartments/shelves, the gripper assembly can easily reach each of the compartments in a fast and accurate manner, while allowing filling the compartments to maximal capacity. In some embodiments, in such settings, the compartments are stationary, i.e., they do not exert a lateral movement between the front and the back faces of the system. In some embodiments, the distance (vertical and/or horizontal) between two consecutive compartments in a column are similar or different. In some embodiments, the distance between the front end of a compartment and the front face of the system is similar, identical or different between two consecutive compartments in a column. In some embodiments, the distance between the front end of a compartment and the front face of the system is similar, identical or different between two compartments in a row.

Reference is now made to FIG. 7A and FIG. 7B, which show a front view and a side view schematic illustrations of an item dispensing system, in accordance with some embodiments of the present invention. FIG. 7A shows a front view schematic illustration of an item dispensing system 700, in accordance with some embodiments of the present invention, of which the front face has been removed, to reveal the internal space of the item dispensing system.

According to some embodiments, the item dispensing system 700 includes a container 722 configured to support a plurality of storage compartments/cells 728a/728b/728c/728d/728e/728f/728g/728h/728i/728j (collectively referred to as storage compartments 728). According to some embodiments, the item dispensing system 700 includes two or more gripper units 762a/762b (collectively referred to as gripper units 762) configured to grip an item, e.g., item 718, positioned within one of the storage compartments/cells 728 and deliver the gripped item to a dispensing outlet 712 of the item dispensing system 700. According to some embodiments, the item dispensing system 700 includes a driving unit configured to drive the one or more gripping units 762. According to some embodiments, the item dispensing system 700 includes a processor configured to control the driving unit.

According to some embodiments, the container 722 includes a lockable box, for example, such as a cabinet or a cupboard. According to some embodiments, the container 722 includes a front side 704 and a back side 706. According to some embodiments, the container 722 is configured to loading and unloading of items from the storage compartments/cells 728 and/or loading and unloading of storage compartments/cells 728 into the container 722. According to some embodiments, the container 722 includes one or more doors along the back side 706 thereof. According to some embodiments, the container 722 includes the dispensing outlet 712. According to some embodiments, the container 722 is configured to contain a plurality of storage compartments/cells 728 wherein each storage compartment is maintained stationary in relation to the container 722. According to some embodiments, the back side 706 of the container 722 optionally includes one or more doors, configured to be opened by a user to allow reaching the internal space of the container 722, for example, to allow loading the compartments with items, for maintenance purposes, and the like. In some embodiments, the item dispensing system includes one or more doors along one or two sides of the system, e.g., a wall positioned normal to the back side 706 and/or the front side 704.

According to some embodiments, the plurality of storage compartments/cells 728 are coupled to the container 722. According to some embodiments, the container 722 includes a holding mechanism, such as, for example, shelfs and/or hooks, configured to maintain a position of the storage compartments/cells 728 in relation to the container 722. According to some embodiments, the holding mechanism is configured such that the storage compartments/cells 728 are removeable from the container 722. According to some embodiments, the storage compartments/cells 728 are arranged within the container 722 as to form rows and/or columns.

According to some embodiments, the storage compartments/cells 728 include a frame configured to support one or more items. According to some embodiments, the storage compartments/cells 728 include a rigid and/or semi-rigid structure. According to some embodiments, different storage compartments/cells 728 include similar or different sizes, shapes, volumes, and/or capacities. For example, in some embodiments, storage compartment designated to hold smaller items may be smaller in volume than storage compartments designated to hold larger items. According to some embodiments, different storage compartments/cells 728 include similar or different compositions, inner dimensions, and/or structural strengths. According to some embodiments, at least a portion of the storage compartments/cells 728 include one or more item storing accessories, such as, for example, shelves, hooks, bins, and/or inner cells.

According to some embodiments, at least a portion of the storages compartments/cells 728 are configured to store one or more items in any desired orientation, such as, for example, in vertical stacks. According to some embodiments, at least a portion of the items 718 include flexible products, textile, newspapers, clothing, including, garments, pants, shirts, scrubs, or any combination thereof. According to some embodiments, at least a portion of the items 718 include a storage bag and/or cover with which the item 718 is stored. According to some embodiments, and as described in greater detail below herein the item dispensing system 700 is configured such that during the dispensing of an item 718, the bag and/or cover of the item 718 is intact and/or undamaged. According to some embodiments, the items 718 stored in at least a portion of the storage compartments/cells 728 is similar, identical or different with respect of quantity (such as number) and/or quality (such as, type, size, color, condition of the item, defects in the item, packaging of the items, and the like, or any combination thereof).

According to some embodiments, and as described in greater detail herein, the storage compartments/cells 728 may include one or more sensors configured to detect an overall quantity of the items within the storage compartments/cells 728. According to some embodiments, the one or more sensors may include a pressure sensor. Advantageously, detecting a quantity of the items enables accurate tracking of the items within the compartments without tracking the number of items that were dispensed using the gripper units and/or through the dispensing outlet 712.

According to some embodiments, the storage compartments/cells 728 includes one or more openings sized to fit at least a portion of the gripper unit 762. According to some embodiments, the one or more openings of the storage compartments are configured such that at least a portion of the gripper unit 762 can enter into the storage compartment/cell 728 and an item 718 positioned within the storage compartment/cell 728. According to some embodiments, the one or more openings extend through one or more walls of the storage compartments/cells 728. According to some embodiments, the one or more openings are defined by the frame of the storage compartments/cells 728.

According to some embodiments, the gripper units 762 are moveably coupled to the container 722. According to some embodiments, the gripper units 762 are moveable within the container 722 in at least two, at least three, at least four, at least five, or at least six degrees of freedom in relation to the container 722. According to some embodiments, and as described in greater detail herein, the gripper units 762 include two or more axes of movement. According to some embodiments, the position and/or spatial orientation of the gripper units 762 is adjustable in relation to the container 722. According to some embodiments, the length and/or shape of the gripper units 762 is adjustable.

According to some embodiments, the gripper units 762 include one or more adjustable portions 770/772 and/or one or more adjustable probes 764a/764b configured to adjust during operation as to grip an item 718 from the storage compartment/cell 728. According to some embodiments, the item dispensing system 700 and/or the driving unit is configured such that an item 718 gripped by the gripper unit 762 is picked up from the storage compartment and then dispensed from the dispensing outlet 712.

According to some embodiments, the gripper units 762 include a first portion 770 coupled to a second portion 772. According to some embodiments, the first portion 770 is moveable in relation to the second portion 772. According to some embodiments, the first portion 770 is coupled to the second portion 772 via coupling mechanism such as, for example, a hinge, rail, and/or gear. According to some embodiments, the first portion 770 is slidable in relation to the second portion 772. According to some embodiments, the first portion 770 and/or the second portion 772 are maintained parallel to one or more of the axes of movement of the gripper units 762. According to some embodiments, the position of the first portion 770 in relation to the second portion 772 is adjustable. According to some embodiments, the position of the second portion 772 in relation to the first portion 770 is adjustable. According to some embodiments, and as described in greater detail herein, the driving unit is coupled to one or more of the first portion 770, the second portion 772, and the coupling mechanism. According to some embodiments, the driving unit is configured to drive a change in position of one or more of the first portion 770 and the second portion 772.

According to some embodiments, the gripper units 762 include one or more probes 764a/764b configured to reach an item placed within a storage compartment/cell 728. According to some embodiments, the one or more probes 764a/764b are configured to clamp, hold, attach, and/or couple to an item positioned within the storage compartment/cell 728. According to some embodiments, the one or more probes 764a/764b include one or more of a rod, a plurality of rods, a clamp, a magnet, and a suction device, or any combination thereof. According to some embodiments the one or more probes 764a/764b are rigid and/or semi rigid. According to some embodiments, the one or more probes 764a/764b are coupled to the second portion 772. According to some embodiments, the one or more probes 764a/764b are coupled to the second portion 772 via a hinge and/or an actuator. According to some embodiments, the hinge and/or the actuator are coupled to the driving unit.

According to some embodiments, the one or more probes 764a/764b are moveable in relation to each other and/or in relation to the first portion 770 and/or the second portion 772. According to some embodiments, and as described in greater detail herein, the driving unit is coupled to the one or more probes 764a/764b. According to some embodiments, the driving unit is configured to drive a change in position and/or spatial orientation of the one or more probes 764a/764b in relation to the first portion 772 and/or the second portion 770.

According to some embodiments, the gripper unit 762 includes an adjustable gripper, having adjustable gripping tense and/or force, and/or adjustable gripping position of the item. According to some embodiments, the gripper unit 762 is customizable. According to some embodiments, the force used by the one or more probes 764a/764b is adjustable, for example, based on the type of item (pants versus shoes), condition of item (folded vs. non-folded, wrapped vs. unwrapped, etc.), number of items in a storage compartment/cell 728 and the like, or any combination thereof. According to some embodiments, the gripper unit 762 includes an adjustable spring configured to translate movement of the one or more probes 764a/764b, thereby enabling an adjustment of the gripping force of the one or more probes 764a/764b.

According to some embodiments, an advantage of having an adjustable gripper unit 762 is in that the gripper unit 762 can be adjusted manually and/or automatically by the command of the processor such that the gripping mechanism of the gripper unit 762 can vary based on, for example, the types of items, at various conditions, in the most accurate, sensitive and fast manner, thereby allowing successfully dispensing a wide variety of items.

According to some embodiments, the gripper units 762 are coupled to one or more gripping assemblies 760. According to some embodiments, one or more gripping assemblies 760 include at least one gripper units 762 coupled thereto. According to some embodiments, one or more gripping assemblies 760 include at least one, at least two, at least three, or at least four gripper units 762. Each possibility is a separate embodiment.

According to some embodiments, the gripper units 762 are moveably coupled to the one or more gripping assemblies 760. According to some embodiments, the gripper units 762 are coupled to one or more gripping assemblies 760 via one or more of a rail, gear, sliding hinge, any combination thereof, and the like. According to some embodiments, two or more gripper units 762 are coupled to one gripping assembly 760. According to some embodiments, each gripper unit 762 is coupled to a single gripping assembly 760. According to some embodiments, each of the gripper units 762 is independently moveable in relation to the gripper assembly 760.

According to some embodiments, the one or more gripping assemblies 760 and/or the one or more gripper units 762 are configured to move along one or more axes of movement. According to some embodiments, the one or more gripping assemblies 760 and/or the one or more gripper units 762 are configured to move along at least one of a vertical axis (X-axis) and a horizontal axis (Y-axis).

According to some embodiments, the axes of movement of the one or more gripping assemblies 760 and/or the one or more gripper units 762 are configured are positioned in close proximity to a wall of the back side 706 of the container 722. According to some embodiments, and as described in greater detail herein, the one or more gripping assemblies 760 and/or the one or more gripper units 762 are coupled to the driving unit such that the driving unit can initiate and/or drive the movement of the one or more gripping assemblies 760 and/or the one or more gripper units 762 are along the one or more axes of movement.

According to some embodiments, the item dispensing system includes one or more gripper assemblies 760 that are each configured to move along a horizontal and/or vertical axis. In some embodiments, two or more gripper assemblies 760 have one or more common axes, such as, for example, a common X-axis and/or a common Y-axis. In some embodiments, two or more gripper assemblies 760 have one or more separate axes, such as, for example, each having a separate X-axis and/or a separate Y-axis.

According to some embodiments, one or more gripper units 762 and/or the gripping assemblies 760 are coupled to one or more driving units configured to drive the one or more gripper units 762 and/or the gripping assemblies 760 at at least one of a fixed speed drive (FSD) and a variable speed drive (VSD). According to some embodiments, the one or more driving units are configured such that when two independent gripper units 762 reach a same and/or coaxial axis of movement, the two gripper units 762 move simultaneously.

According to some embodiments, the one or more gripping assemblies 760 and/or the one or more gripper units 762 are coupled to the driving unit via one or more actuating units 766a/766b (collectively referred to hereinafter as one or more actuating units 766). According to some embodiments, the one or more actuating units 766 include one or more of a motor, arm, piston, rail, shaft, cable, screw, a pully, or any combination thereof. According to some embodiments, the one or more actuating units 766 enable a coordinated movement of the one or more gripping assemblies 760 and/or the one or more gripper units 762 are at least along the one or more axes of movement, such as, for example, the horizontal axis and the vertical axis in relation to the container 722.

According to some embodiments, each of the gripper units 762 and/or the gripping assemblies 760 may have an independent corresponding actuating unit. In some embodiments, common elements of the actuating unit (such as a motor) may be shared between individual actuating units. In one embodiment, the movement of the one or more gripper units 762 and/or the one or more gripping assemblies 760 may be actuated, at least partially using one or more pistons, which may be placed on a rail, such as, for example, rails 714. In a starting/resting position, the one or more ripper units 762 and/or the one or more gripping assemblies 760 are located in close proximity to the back side 706 of the item delivery system 700. When dispensing an item is initiated, the one or more gripper units 762 and/or the one or more gripping assemblies 760 may move towards one or more of the storage compartments/cells 728, where the item is situated.

According to some embodiments, two or more gripping assemblies 760 and/or two or more gripper units 762 are simultaneously moveable along one or more axes of movement. According to some embodiments, two or more gripping assemblies 760 and/or two or more gripper units 762 are simultaneously moveable along the same axis of movement. According to some embodiments, two or more gripping assemblies 760 and/or two or more gripper units 762 are simultaneously moveable along the same rail 714. According to some embodiments, two or more gripping assemblies 760 and/or two or more gripper units 762 are simultaneously moveable along different axis of movement. According to some embodiments, and as described in greater detail herein, the processor is configured to control the driving unit such that two or more gripping assemblies 760 and/or two or more gripper units 762 are simultaneously movable in a same and/or different directions.

According to some embodiments, the processor is configured to control the driving unit such that two or more gripping assemblies 760 and/or two or more gripper units 762 are simultaneously directed towards different storage compartments/cells 728. According to some embodiments, the processor is configured to control the driving unit such that two or more gripping assemblies 760 and/or two or more gripper units 762 are simultaneously gripping two or more different items, wherein each item originates from a separate storage compartment/cell 728. According to some embodiments, the processor is configured to control the driving unit such that one or more gripping assemblies 760 and/or two or more gripper units 762 are configured to simultaneously dispense two or more different/separate items, wherein each item originates from a separate storage compartment/cell 728.

According to some embodiments, the item dispensing system includes an item counting mechanism configured to count, calculate, and/or keep track of the quantity of items within one or more of the storage compartments/cells 728 of the item dispensing system 700. According to some embodiments, the item counting mechanism is in communication with the memory module of the item dispensing system 700. According to some embodiments, the memory module of the item dispensing system 700 includes data associated with one or more of a dimension, height, and/or volume of one or more of the storage compartments/cells 728. According to some embodiments, the memory module includes data associated with one or more of a dimension, height, and/or volume of the one or more items within the storage compartments/cells 728. According to some embodiments, and as described in greater detail herein, one or more of the storage compartments and/or the items include a tag and/or marker including data associated with at least one of a dimension, height, and/or volume of the storage compartment/cell 728 and/or a dimension, height, and/or volume of the item.

According to some embodiments, during operation of the gripper unit 762, at least a portion of the gripper unit 762 enters a storage compartment 728. According to some embodiments, the processor is configured to measure a time of operation of the gripper unit 762 within the storage compartment/cell 728. According to some embodiments, the processor is configured to measure a distance traveled and/or translated by the gripper unit 762 within the storage compartment/cell 728. According to some embodiments, the processor is configured to calculate number of items remaining in the storage compartment. According to some embodiments, the processor is configured to calculate a number of items remaining in the storage compartment/cell 728, based, at least in part, on at least one of the data associated with one or more of a dimension, height, and/or volume of the one or more items, the data associated with a dimension, height, and/or volume of one or more of the storage compartments 728, the measured distance traveled and/or translated by the gripper unit 762 within the storage compartment/cell 728, and the time of operation of the gripper unit 762 within a storage compartment/cell 728. According to some embodiments, the processor is configured to calculate a number of items remaining in the storage compartment/cell 728, based, at least in part, on the measured distance traveled and/or translated by the gripper unit 762 within the storage compartment/cell 728. According to some embodiments, the processor is configured to receive and/or calculate a height of the top item in a stack of items contained in a storage compartment/cell 728, based, at least in part, on a marker and/or tag configured to be detected using a sensor and/or RFID, and the measured time and/or distance of travel of a gripper unit 762 during a dispensing of an item from the storage compartment/cell 728.

According to some embodiments, the memory module is configured to store data associated with a height of the top item in a stack of items contained in a storage compartment/cell 728. According to some embodiments, the processor is configured to update the data stored within the memory module each item is removed. According to some embodiments, the processor is configured to calculate a travel distance for a gripper unit 762 within a compartment/cell 728 based, at least in part, on the data associated with the height of the top item in a stack of items contained in a storage compartment/cell 728 and/or a number of removed items from the storage compartment/cell 728.

According to some embodiments, the processor is configured to pre-plan a rout of operation of the one or more gripper units 762, based, at least in part, on at least one of the calculated number of items remaining in the storage compartment/cell 728, the data associated with one or more of a dimension, height, and/or volume of the one or more items and/or one or more of the storage compartments/cells 728, the measured distance traveled and/or translated by the gripper unit 762 within the storage compartment/cell 728, and the time of operation of the gripper unit 762 within a storage compartment/cell 728. According to some embodiments, the processor is configured to pre-plan a rout of operation of the one or more gripper units 762 based, at least in part, on the height of the top item in the stack currently stored in a storage compartment/cell 728.

According to some embodiments, and as described in greater detail herein, the item dispensing system 700 includes an inventory management assembly configured to calculate the number of items within the storage compartments/cells 728. According to some embodiments, the inventory management assembly is configured to keep track of the total number of dispensed items from the storage compartments/cells 728. According to some embodiments, the inventory management assembly is coupled to and/or is in communication with the processor. According to some embodiments, the inventory management assembly is configured to receive, obtain, and/or calculate a number of the items in a storage compartment/cell 728 based, at least in part, on data associated with a height of the top item in a stack of items contained in a storage compartment/cell 728.

According to some embodiments, the item dispensing system 700 may include one or more sensors positioned within the container 722 and configured to detect movement of the two or more gripper units 762 and/or two or more gripping assemblies 760. According to some embodiments, a processor may be in communication with the one or more sensors. According to some embodiments, the processor is configured to command an operation of the two or more gripper units 762 and/or two or more gripping assemblies 760 in separate paths of movement, thereby preventing collision of the two or more gripper units 762 and/or two or more gripping assemblies 760.

Reference is made to FIG. 8A, FIG. 8B, and FIG. 8C, which are front view schematic illustrations of an item dispensing system at three separate stages of operation during dispatchment of two items from two storage compartments of an item dispensing system, in accordance with some embodiments of the present invention.

According to some embodiments, such as depicted in FIG. 8A, FIG. 8B, and FIG. 8C, item dispensing system 700/800 includes one or more additional rails 814a/814b/814c/814d/814e (referred to hereinafter as one or more additional rails 814) positioned within the container 722 and configured to support one or more axes of movement of the one or more gripper units 762 and/or the gripping assemblies 760. According to some embodiments, the one or more additional rails 814 are normal to and/or angled in relation to the rails 714. According to some embodiments, the one or more additional rails 814 are coupled to the rails 714 such that the one or more gripper units 762 and/or the gripping assemblies 760 can transfer from one of the rails 714 to one or more of the additional rails 814, and vice versa. According to some embodiments, the rails 714 and/or the additional rails 814 form a grid configured to support movement of the gripper units 762 and/or the gripping assemblies 760 along one or more planes defined by the grid. According to some embodiments, the one or more rails 714, the one or more additional rails 814, and/or the grid define a path of movement for the one or more gripper units 762 and/or the gripping assemblies 760. According to some embodiments, the path includes a plurality of planes. According to some embodiments, the gripper units 762 and/or the gripping assemblies 760 are moveable along the one or more rails 714, the one or more additional rails 814, and/or the grid.

According to some embodiments, the one or more rails 714 and/or the one or more additional rails 814 may be connected permanently or via connecting elements such as, hinges, allowing at least some degree of movement between one or more of the rails 714 and/or the additional rails 814. According to some embodiments, one or more gripper unit 762 and/or gripping assembly is coupled to the one or more rails 714 and/or additional rails 814 via hinges, thereby enabling at least one degree of freedom to the adjustable gripper unit 762 in relation to the rail 714 and/or the additional rail 814.

Reference is made to FIG. 9, which is a flowchart of functional steps in a method for simultaneously dispensing a plurality of items from an item dispensing system, in accordance with some embodiments of the present invention.

According to some embodiments, the method 900 includes receiving user input from the user interface 102, wherein the user input is associated with a plurality of items desired for dispensing from an item dispensing system, such as item dispensing system 900. It is understood that the method 900 may be associated with a plurality of items desired for dispensing from any of the disclosed item dispensing systems herein, such as 100/600/700/800.

According to some embodiments, the method 900 includes identifying a location of the plurality of items within the container 722. According to some embodiments, at step 902, the method includes identifying a plurality of storage compartments associated with two or more items. According to some embodiments, the method 900 includes identifying storage compartments/cells 728 containing/holding the plurality of selected items. According to some embodiments, for a case in which the plurality of items is positioned in two or more different storage compartments 728, the method 900 includes identifying each of the storage compartments/cells 728 which contain the items desired for dispensing. According to some embodiments, when more than one storage compartment/cell 728 includes a same single item or type of item desired for dispensing, the method 900 includes choosing one storage compartment from which the item will be dispensed. According to some embodiments, the method 900 includes choosing one storage compartment/cell based, at least in part, on a route of the gripper unit 762 and/or gripping assembly 760 towards the chosen/selected storage compartment. According to some embodiments, the method 900 includes choosing/selecting one storage compartment based, at least in part, on a route of a gripper unit 762 and/or gripping assembly 760 towards a different storage compartment for dispensing of a second and/or different/separate item, such that the paths of the two or more gripper units 762 and/or gripping assemblies 760 do not collide or intersect. According to some embodiments, the method 900 may include calculating a time for each route and/or combination of routes of the two or more gripper units 762 and/or gripping assemblies 760 associated with dispensing the plurality of items. According to some embodiments, the method 900 includes choosing one or more storage compartments associated with a same desired item based, at least in part, on the fastest/time efficient calculated route.

According to some embodiments, at step 904, the method may include moving two or more gripper units 762 and/or gripping assemblies 760 to the plurality of identified storage compartments. According to some embodiments, the method 900 includes moving the two or more gripper units 762 and/or corresponding gripping assemblies 760 along one or more axes of movements. According to some embodiments, the method 900 includes moving the two or more gripper units 762 and/or gripping assemblies 760 along at least one of a horizontal axes and/or a vertical axis, or any combination thereof. According to some embodiments, the method 900 includes moving the two or more gripper units 762 and/or gripping assemblies 760 along one or more of the rails 124, the additional rails 814, and the grid, or any combination thereof. According to some embodiments, the method 900 includes adjusting at least one of a position and a spatial orientation of the gripper units 762 and/or gripping assemblies 760 in relation to the container 722. According to some embodiments, the method 900 includes adjusting the length and/or shape of the gripper units 762. According to some embodiments, the method 900 includes adjusting the position of the first portion 770 of the gripper unit 762 in relation to the second portion 772 of the gripper unit 762. According to some embodiments, the method 900 includes adjusting the position of the second portion 772 of the gripper unit 762 in relation to the first portion 770 of the gripper unit 762.

According to some embodiments, the method 900 includes adjusting the positions of the one or more probes 764 in relation to the second portion 722 of the gripper unit. According to some embodiments, the method 900 includes adjusting the positions of the one or more probes 764 such that an item can fit between two or more of the probes 764 of a gripper unit 762. According to some embodiments, the method 900 includes gripping an item from the identified storage compartment/cell 728 using the one or more probes 764 of the gripper unit 762.

According to some embodiments, the operation of one or more gripper units 762 and/or gripping assemblies 760 is simultaneous or at least semi-simultaneous to other operations of other gripper units 762 and/or gripping assemblies. According to some embodiments, the method 900 includes operating two or more gripper units 762 and/or gripping assemblies 760 simultaneously, semi-simultaneously/consecutively. According to some embodiments, the two or more gripper units 762 and/or gripping assemblies 760 which are operated simultaneously may include different operational steps, such as, for example, different paths towards different identified storage compartments/cells 728, different adjustments of the gripper unit 762, different adjustments of the probes 764 due to different types of items to be dispensed. According to some embodiments, two or more gripper units 762 and/or gripping assemblies may be in operation at different stages of the dispensing process.

For example, according to some embodiments, such as depicted in FIG. 8B, during one of the exemplary stages of operation of the item dispensing system 800, one of the gripper units 762*a* has reached a designated storage compartment/cell 728*b* and has begun gripping an item from the storage compartment 728*b*, while at the same time, the second gripper unit 762*b* has only then reached the designated storage compartment 728*h*. FIG. 8C shows an exemplary stage of operation following that of the stage depicted by FIG. 8B, in which one of the gripper units 762*a* has picked up the designated item from storage compartment/cell 728*b* while the second gripper unit 762*b* has begun gripping a designated item from storage compartment 728*h*.

According to some embodiments, the method 900 may include lifting/picking an item from the identified storage compartment. According to some embodiments, the method 900 includes selecting a specific item within the storage compartment 728. According to some embodiments, at step 906, the method 900 includes removing one or more items from the identified storage compartments. According to some embodiments, the method 900 includes carrying the item towards the dispensing outlet 712, using the one or more gripper units 762 and/or the gripping assemblies 760. According to some embodiments, at step 908, the method 900 includes dispensing the items, using the two or more gripper units and/or gripping assemblies, through a dispensing outlet, wherein the plurality of items are dispensed together, essentially at the same time.

According to some embodiments, the item dispensing system 100/700/800 may further include an inventory management assembly, which may include, inter alia, a processing module and one or more sensors to determine (directly or indirectly) various parameters related to the items stored in the various storage compartments 728. In some embodiments, exemplary sensors may include, for example, but not limited to: spatial sensors, temporal sensors, visual sensors, weight sensors, remote sensors, such as RFID sensors, and the like, or any combinations thereof. In some embodiments, the sensors may include, for example, a timer, an optical imager, such as a camera, a motor and encoder, servomotor, step motor, scale, RFID antenna, and the like, or any combination thereof.

According to some embodiments, the system may utilize Radio-Frequency (RF) means as sensors to detect and identify various quantity and/or quality parameters of the items stored and dispensed. In some embodiments, the item dispensing systems 700/800 may include one or more RFID readers (antennas) of various intensities. The RFID reader may be placed/located in various regions of the item dispensing system 100/700/800. For example, in some embodiments, the RFID antennas may be located in close proximity to the item dispensing system 100/700/800, for example, in the channel of the dispensing outlet 712. In some embodiments, the RFID reader may be placed in or in close proximity to one or more of the storage compartments/cells 728. In some embodiments, a central RFID reader may be located/positioned in the item dispensing system 700/800, at any desired position (not necessarily in the channel or in close proximity to the dispensing outlet 712), which can read/identify the entire content of items (having an RFID tag) stored in the item dispensing system 100/700/800. In some embodiments, the RFID reader may be stationary. In some embodiments, the RFID reader may be moveable. In some embodiments, a combination of stationary and moveable RFID readers may be used. In some embodiments, the RFID reader may be moveable by one or more arms or moving platforms, that can allow changing the location of the RFID reader. In some embodiments, the RFID reader may be placed on or in close proximity to the one or more gripping assemblies 760 and may optionally move in coordination with the one or more gripper units 762.

According to some embodiments, one or more of the storage compartments/cells 728 may further include an indication as to the inventory condition of the items in the storage compartment/cell 728. For example, a light sensitive or light reflective tag may be placed in a compartment, whereby if light is reflected from the tag, it is indicative that a storage compartment/cell 728 is empty. In some embodiments, the indicator may be a visual indicator, such as a LED light, which is lit when the number of items in a storage compartment/cell 728 is below a threshold. Such an indication may be visualized by a technician, indicating which storage compartments/cells 728 need to be filled.

According to some embodiments, the one or more storage compartments/cells 728 and/or one or more items may include a tag and/or marker configured to be identified by one or more sensors during operation of the one or more gripper units 762 and/or gripping assemblies 760. According to some embodiments, the tag and/or marker may include data associated with a type of item within a container 722. According to some embodiments, the tag and/or marker may include data associated with a type of item having the tag and/or marker. A potential advantage of the tag and/or marker including data associated with a specific type of item is in that the processor receiving a signal from the sensor, wherein the signal is associated with a detected tag and/or marker of the item, may command a specified adjustment to the gripper unit 762. For example, according to some embodiments, the processor may command an adjustment to the gripper unit 762 such that a specified item is gripped with a pre-calculated force, and/or at a predetermined location on the item.

In some embodiments, one or more of the storage compartments/cells 728 may include means for holding or securing the items in the storage compartments/cells 728, inducing, for example, rubber bands, friction regions, and the like. According to some embodiments, as detailed above, the item dispensing system 100/700/800 may further include a returned item compartment prior to dispensing, for quality assurance issues related to the dispensing: for example, if the item dispensing system 100/700/800 and/or the processor (not shown) identified an item without RFID tag, damaged items, two items gripped instead of one, and the like, such items will not be dispensed via the item dispensing system 100/700/800, but rather removed to the returned item compartment.

According to some embodiments, as detailed herein, the item dispensing system 100/700/800 may further include a disinfection/cleaning unit, including, for example, but not limited to: a UV unit, microwave unit, vacuum unit, air circulation unit, and the like, or any combination thereof. According to some embodiments, as detailed herein, the system may further include a back collection chamber, for collection of falling items, and the like, to prevent the gripper units 762 and/or the gripping assemblies 760 from getting stuck and thereby allow smooth and uncompromised operation of the item dispensing system 100/700/800.

According to some embodiments, the item dispensing system 100/700/800 may include one or more locking mechanisms, preventing the opening of the front and/or back side, while the item dispensing system 100/700/800 is operating.

According to some embodiments, the gripper unit 762 includes one or more sensors configured to provide indication regarding the items to be gripped. In some embodiments, the sensors may include a proximity sensor and an RFID reader. According to some embodiments, one or more of the storage compartments/cells 728 include one or more sensors configured to provide indications regarding inventory of items.

According to some embodiments, the RFID reader includes an RFID antenna positioned in close proximity to the dispensing outlet 712, configured to detect/identify a corresponding RFID Tag of a dispensed item. According to some embodiments, the item dispensing system 100/700/800 may further include an internal collection chamber configured to collect items that were gripped but were not dispensed via the dispensing outlet 712. According to some embodiments, items that were gripped but were not dispensed include: damaged items, items having a defective RFID tag, items missing an RFID tag, multiple gripped items, or any combination thereof.

According to some embodiments, the item dispensing system 100/700/800 may further include a disinfecting and/or cleaning unit. According to some embodiments, the disinfecting and/or cleaning unit may include one or more of: a UV disinfection unit, a microwave disinfecting unit, a vacuum unit, an air circulation unit, or any combination thereof. In some embodiments, the disinfecting unit/cleaning unit is located on the top portion of the item dispensing system 100/700/800.

According to some embodiments, the advantageous item dispensing system 100/700/800 disclosed herein is user friendly, cost effective and environmentally friendly, as the item dispensing system 100/700/800 consumes less energy, exhibits fast item dispensing/delivery time, requires less space, operates quietly (less noise), has larger capacity, as the storage compartments/cells 728 may be filled to the top, has an increased variety of items, and the like.

According to some embodiments, the item dispensing system 100/700/800 disclosed herein exhibits faster item dispensing time as compared to other item dispensing systems, in particular with respect of dispensing sets or items. In some embodiments, the dispensing systems disclosed herein exhibit an improvement of at least about 50-60%, at least about 60-70%, at least about 70-80%, at least about 80-90%, or at least about 90-100% in dispensing time of the plurality of items. In some embodiments, the dispensing systems disclosed herein exhibit an improvement of at least over about 90% in dispensing time of plurality of items (i.e., set of items).

As used herein, the term "set" is directed to a plurality of items (for example, two items, two or more items, three or more items) that are dispensed together. In some embodiments, each item in a set is placed/stored in a different cell/compartment. In some embodiments, at least one item of a set of three or more items is placed/stored in a different cell/compartment as the other items. For example, a set of items may include pants and shirt (having the same or different size and/or color). For example, a set of items may include two shirts (having the same or different size and/or color). For example, a set of items may include two pants (having the same or different size and/or color). For example, a set of items may include two shirts and two pants.

According to some embodiments, the item dispensing system 100/700/800 may further include one or more cartridges configured to contain one or more items. According to some embodiments, the one or more cartridges are configured to be placed within one or more storage compartments/cells 728. In some embodiments, the one or more cartridges are configured to be placed onto one or more shelves. In some embodiments, the cartridges may include a marker, a sensor, and/or a tag which can be read by a sensor of the item dispensing system during loading of the cartridges into the storage compartments/cells 728 and/or shelves. In some embodiments, the item dispensing system 100/700/800 may include one or more sensors, such as, for example, the RFID reader, configured to detect the marker, sensor, and/or tag of the cartridge. In some embodiments, the item dispensing system 100/700/800 may include an indicator, such as a sound and/or optical indicator, configured to indicate to a user which compartment is associated with a detected cartridge.

According to some embodiments, the items may include a marker, a sensor, and/or a tag which can be read by a sensor of the item dispensing system 100/700/800. In some embodiments, the item dispensing system 100/700/800 may include one or more sensors, such as, for example, the RFID reader, configured to detect the marker, sensor, and/or tag of the items during loading of the items into the item dispensing system 100/700/800. In some embodiments, the system may include an indicator, such as a sound and/or optical indicator, configured to indicate to a user which storage compartment/cell 728 is associated with a detected item.

According to some embodiments, the back collection chamber may be coupled to the dispensing outlet 712 such that a user may return an item by inserting the item back into the dispensing outlet 712. In some embodiments, the back collection chamber may include a collection outlet separate from the dispensing outlet 712 and configured to allow a user to return an item into the back collection chamber. In some embodiments, the back collection chamber is in communication with at least one of the dispensing outlet 712 and the collection outlet. In some embodiments, at least one of the dispensing outlet 712 and the collection outlet is in fluid communication with a channel configured to direct an item to the back collection chamber. In some embodiments, at least one of the dispensing outlet 712 and the collection outlet include a moveable shelf configured to support a returned item at a closed position of the moveable shelf. In some embodiments, at a closed position, the moveable shelf is configured to block an item from entering the channel. In some embodiments, at an open position, the moveable shelf is configured to collapse such that an item supported by the moveable shelf enters the channel.

According to some embodiments, the shelf is coupled to a compartment configured to contain a returned item. In some embodiments, the compartment is configured to limit the dimensions of the returned items. In some embodiments, for a flexible item, the compartment is configured to compress the item. Advantageously, compression of an item before the collapse of the moveable shelf enables an efficient use of the space within the system and/or within the back collection compartment. According to some embodiments, the system includes a sweeper configured to push and/or direct the returned item from the shelf to the channel and/or the back collection compartment.

Reference is now made to FIG. 10A and FIG. 10B, which are front view schematic illustrations of a returning unit at two stages of operation during compression of returned items, in accordance with some embodiments of the present disclosure.

According to some embodiments, FIG. 10A and FIG. 10B depict a front face 1004 of a returning unit 1000. According to some embodiments, front face 1004 may include a user interface 1002, which allows a user to interact with returning unit 1000. According to some embodiments, user interaction with returning unit 1000 may be performed via a user interface of the disclosed herein item dispensing system, such as, but limited to, item dispensing system 700. Put differently, in some embodiments returning unit 1000 may be included or associated with an item dispensing unit, such as item dispensing unit 700. In some embodiments, returning unit 1000 may be an independently operated unit (i.e. not associated with an item dispensing system). In some embodiments, the returns unit may be physically and/or functionally associated with an item dispensing unit/system.

According to some embodiments, user interface 1002 may include any type of user interface, including, for example, but not limited to: keyboard, monitor, screen, display, touch-screen, vocal activated interface, face recognition interface, use of QR code, smartphone application, and the like. According to some embodiments, user may interact with user interface 1002 for identity authentication (e.g. by receiving an employee number) and inventory management. According to some embodiments, user interface 1002 may notify and/or confirm the number and the type of the collected items by returning unit 1000. According to some embodiments, user interface 1002 may notify users, such as by displaying messages on a screen. According to some embodiments, notifications displayed on the user interface 1002 may include information regarding the available storage volume, maintenance-related information, and the like.

According to some embodiments, returning unit 1000 includes an opening 1012 for disposing the items by a user. According to some embodiments, opening 1012 may be configured to open upon request. As a non-limiting example, returning unit 1000 may be configured to collect the returned items upon confirming user-related information (e.g. employee number, full name, verification code, and the like).

According to some embodiments, the returned items may include any type of items, such as, for example, any type of clothing, including, garments, pants, shirts, scrubs, aprons, lab coats, doctor coats, and the like, or any combination thereof. According to some embodiments, the returned items may include used items, such as used clothing.

According to some embodiments, returning unit 1000 may include a movable shelf 1021 configured to allow storing/accumulating of the retuned items. According to some embodiments, movable shelf 1021 may move towards (i.e. outwards of front face 1004) to facilitate the access to the returned items (e.g. for collecting/emptying of the retuning unit 1000). According to some embodiments, movable shelf 1021 may be disassembled from returning unit 1000 (e.g. by releasing locking screws and/or pushing forward the movable shelf 1021).

According to some embodiments, returning unit 1000 may include a compacting unit/kit 1050. According to some embodiments, compactor kit 1050 may include a compactor 1080 configured to compress a returned items (e.g. compressing a pile of items 1020, as depicted in FIG. 10A and FIG. 10B). Thus, advantageously minimizing the volume of the returned items, which, in turn, leads to increasing the capacity and the availability of returning unit 1000. According to some embodiments, compacting kit 1050 may increase the capacity of the returning unit 1000 by about 50-150%, such as, 80%, 90% and 100%. As a non-limiting example, the capacity of the returning unit 1000 may be increased, for example, from collecting 160-200 returned items to collecting 380-400 returned items.

According to some embodiments, compactor 1080 may include a first panel 1084, a second panel 1086, and a rail 1082, such that the second panel 1086 is configured to move upwards and downwards (i.e. extend) relative to the first panel 1084. In some embodiments, the movement is facilitated by a piston mechanism. According to some embodiments, compactor 1080 may include a base 1088 (e.g. a metal frame) configured to compress the returned items, for example, by applying pressure on the returned items (for example, on a pile of returned items). According to some embodiments, base 1088 may be planar. According to some embodiments, base 1088 may be angular. According to some embodiments and as depicted in FIG. 10A and FIG. 10B, base 1088 may include one or more hinges 1090, configured to allow changing the configuration of base 1088, such as, for example, allowing an angled configuration. In some embodiments, angled configuration may facilitate compressing of the returned items and minimize the storage space of the folded configuration of compactor 1080. In some embodiments, the hinges may allow adjusting of base, such as but limited to configuration and/or angle adjustment thereof.

According to some embodiments, compactor 1080 may include one or more connectors configured to connect compactor 1080 to a returning unit (e.g. frame of the returning unit). According to some embodiments, compactor 1080 may include one or more supporting panels configured to secure and optionally enable locking of the compactor and/or base.

According to some embodiments, compactor 1080 may include a motor allowing a controlled movement of first panel 1084 and/or second panel 1086.

According to some embodiments, compactor 1080 may include or be associated with one or more sensors (not shown) and actuators. According to some embodiments, one or more sensors may be configured to detect the volume (e.g. height of pile 1020) of the returned items. According to some embodiments, returning unit 1000 may include one or more sensors, such as weight sensors, proximity sensor, distance sensor, and the like, configured to evaluate/measure the weight/amount/size of the returned items.

According to some embodiments, one or more sensors may communicate with a controller, which, in turn, controls the operation of the compactor, i.e., the compression performed by compactor 1080. As a non-limiting example, compactor 1080 may be configured to perform the compression of the returned items upon request (e.g. when the movable shelf 1021 is determined to be full). According to some embodiments, compactor 1080 may perform compressing of the returned items periodically (such as but not limited to, every 50, 80, 100, 120 or more item returns). In some embodiments, the compactor may be configured to perform compression of the returned items, based on input from the one or more sensors. In some embodiments, the compactor may operate automatically, semi-automatically and/or manually, in accordance with the user preference.

According to some embodiments, compactor 1080 may be operated manually by a user, for example, via a user interface. According to some embodiments, the position of compactor 1080 within the return unit may be displayed on user interface 1002.

According to some embodiments, returning unit 1000 may include a scanner (not shown). According to some embodiments, the scanner may include one or more of: X-ray scanning, a millimeter wave scanner, and the like. Different scenarios wherein in might be beneficial to scan the returned items may include counting the returned items, evaluating the condition of the returned items, and detecting concealed or foreign objects.

According to some embodiments, returning unit 1000 may further include disinfecting and/or cleaning unit. According to some embodiments, the disinfecting and/or cleaning includes one or more of: illumination disinfecting (such as UV disinfecting), microwave disinfecting, vacuuming, circulating air, chemical-assisted disinfecting, or any combination thereof.

According to some embodiments, the operation logic/process of the compactor may include one or more of the following steps: before any activity—check for safety interlock and confirm the main door is closed; Turn the item drop shelf (i.e. the shelf of the returning unit chute)[until it reaches the shelf sensor (that may be located, for example on the frame of the return unit, on the drop shelf, on the compactor, and the like); If an item remains in the return cell/region, turn the shelf again (up to three times); perform an actuator cycle, including, Move actuator down (stop on down sensor or down Time-Out), Move actuator up (stop on up sensor or up Time-Out), If stop on up Time-Out, retry actuator cycle one more time, If stop on up Time-Out for the second time, the compactor (in particular, the actuator) is disabled until the next BIT After each standard shelf cycle, check if 'unit is full' has been detected, Turn the shelf (again) unit it reaches the shelf sensor, perform an actuator cycle, if it is detected again that the unit is full, repeat actuator cycle. In some embodiments, during the logic process, the programmable logic controller PLC does not receive an indication that the return unit (station) is full, and only after the process is ended, if the unit is still determined to be full, the user receive an indication that the unit (station) is full.

According to some embodiments, the systems disclosed herein may utilize, any type of suitable motors, such as, AC motors, DC motors, and the like. In some embodiments, the motors may be selected from brushless and brushed motors. In some embodiments, the motors may be selected from: AC induction motors, brushless AC motors, AC motors with permanent magnetic fields, and the like. In some embodiments, the systems may include one or more encoders, such as, rotary and linear encoders.

According to some embodiments, the dispensing system may further include an inventory management assembly, which may include, inter alia, a processing module and one or more sensors to determine (directly or indirectly) various parameters related to the items stored in the various compartments. In some embodiments, exemplary sensors may include, for example, but not limited to: spatial sensors, temporal sensors, visual sensors, weight sensors, remote sensors, such as RFID sensors, and the like, or any combinations thereof. In some embodiments, the sensors may include, for example, a timer, an optical imager, such as a camera, a motor and encoder, servomotor, step motor, scale, RFID antenna, and the like, or any combination thereof.

According to some embodiments, the system may utilize Radio-Frequency (RF) means as sensors to detect and identify various quantity and/or quality parameters of the items stored and dispensed. In some embodiments, the system may include one or more RFID readers (antennas) of various intensities. The RFID reader may be placed/located in various regions of the dispensing system. For example, in some embodiments, the RFID antennas may be located in close proximity to the item dispensing unit, for example, in the chute of the dispensing unit. In some embodiments, the RFID reader may be placed in or in close proximity to one or more of the compartments. In some embodiments, a central RFID reader may be located/positioned in the system, at any desired position (not necessarily in the chute or in close proximity to the outlet), which can read/identify the entire content of items (having an RFID tag) stored in the dispensing system. In some embodiments, the RFID reader may be stationary. In some embodiments, the RFID reader may be moveable. In some embodiments, a combination of stationary and moveable RFID readers may be used. In some embodiments, the RFID reader may be moveable by one or more arms or moving platforms, that can allow changing the location of the RFID reader. In some embodiments, the RFID reader may be placed on or in close proximity to the gripper assembly and may optionally move in coordination with the gripper unit.

According to some embodiments, one or more of the compartments may further include an indication as to the inventory condition of the items in the compartment. For example, a light sensitive or light reflective tag may be placed in a compartment, whereby if light is reflected from the tag, it is indicative that the compartment is empty. In some embodiments, the indicator may be a visual indicator, such as a LED light, which is lit when the number of items in a compartment is below a threshold. Such an indication may be visualized by a technician, indicating which compartments needs to be filled. In some embodiments, one or more of the compartments may include means for holding or securing the items in the compartment, inducing, for example, rubber bands, friction regions, and the like.

According to some embodiments, loading/placing items in the system may be performed using dedicated cartridges or carts, that may be placed in the system, for example, in one or more compartments. Using such cartridges or carts may enhance the loading of the system with items. Enhancing loading may be cost and/or time efficient, as compared to loading individual items. In some embodiments, loading the system with items using cartridges or carts may be performed via any one of the loading doors/regions of the system, including, for example, front, back or sides.

According to some embodiments, the system may further include one or more cartridges configured to contain one or more items or types of items. According to some embodiments, the one or more cartridges are configured to be placed within one or more compartments. In some embodiments, the one or more cartridges are configured to be placed onto one or more shelves. In some embodiments, the cartridges may include a marker, a sensor, and/or a tag which can be read by a sensor of the system during loading of the cartridges into the compartments and/or shelves. In some embodiments, the system may include one or more sensors, such as, for example, the RFID reader, configured to detect the marker, sensor, and/or tag of the cartridge. In some embodiments, the system may include an indicator, such as a sound and/or optical indicator, configured to indicate to a user which compartment is associated with a detected cartridge. According to some embodiments, the items may include a marker, a sensor, and/or a tag which can be read by a sensor of the system. In some embodiments, the system may include one or more sensors, such as, for example, the RFID reader, configured to detect the marker, sensor, and/or tag of the items during loading of the items into the system. In some embodiments, the system may include an indicator, such as a sound and/or optical indicator, configured to indicate to a user which compartment is associated with a detected item.

According to some embodiments, as detailed above, the system may further include a return collection chamber prior to dispensing, for quality assurance issues related to the dispensing: for example, if the dispensing system identified an item without RFID tag, damaged items, two items gripped instead of one, and the like, such items will not be dispensed via the dispensing unit, but rather removed to the return collection chamber.

According to some embodiments, as detailed herein, the system may further include a disinfection/cleaning unit, including, for example, but not limited to: a UV unit, microwave unit, vacuum unit, air circulation unit, and the like, or any combination thereof.

According to some embodiments, as detailed herein, the system may further include a back collection chamber, for collection of falling items, and the like, to prevent the front shelves/compartments from getting stuck and thereby allow smooth and uncompromised operation of the dispending system.

According to some embodiments, the back collection chamber may be coupled to the dispensing outlet such that a user may return an item by inserting the item back into the dispensing outlet. In some embodiments, the back collection chamber may include a collection outlet separate from the dispensing outlet and configured to allow a user to return an item into the back collection chamber. In some embodiments, the back collection chamber is in communication with at least one of the dispensing outlet and the collection outlet. In some embodiments, at least one of the dispensing outlet and the collection outlet is in fluid communication with a channel configured to direct an item to the back collection chamber. In some embodiments, at least one of the dispensing outlet and the collection outlet include a moveable shelf configured to support a returned item at a closed position of the moveable shelf. In some embodiments, at a closed position, the moveable shelf is configured to block an item from entering the channel. In some embodiments, at an open position, the moveable shelf is configured to collapse such that an item supported by the moveable shelf enters the channel. According to some embodiments, the shelf is coupled to a compartment configured to contain a returned item. In some embodiments, the compartment is configured to limit the dimensions of the returned items. In some embodiments, for a flexible item, the compartment is configured to compress the item. Advantageously, compression of an item before the collapse of the moveable shelf enables an efficient use of the space within the system and/or within the back collection compartment. According to some embodiments, the system comprises a sweeper configured to push and/or direct the returned item from the shelf to the channel and/or the back collection compartment.

According to some embodiments, the system may include one or more locking mechanisms, preventing the opening of the front and/or back side, while the system is operating.

According to some embodiments, at least one of the shelve(s) may be configured to move and protrude out of the container (from the back face or front face, when the respective door is open), to allow easy access to an operator for loading the shelve(s) with items.

According to some embodiments, there is thus provided an item dispensing system which includes: a container having a front face and a back face, the container includes:
- a plurality of storage compartments configured for storage/holding of items, wherein the storage compartments are arranged in one or more sets, each set is arranged in rows and/or columns, wherein each of the sets of the storage compartments is configured to move laterally between the front face and the back face of the container; and
- a gripper assembly configured to move along a vertical axis and/or a horizontal axis, said gripper assembly includes at least one adjustable gripper configured to allow an adjustable gripping of an item in a designated storage compartment and deliver the gripped item to a dispensing outlet;
- wherein the lateral movement of the set of compartments and the movement of the gripper assembly is coordinated to thereby allow temporal and spatial accurate positioning of the adjustable gripper and the designed compartment.

According to some embodiments, the adjustable gripper has at least two opposing movable arms, configured to adjustably grip an item, based on the characteristics of the item in the compartment.

According to some embodiments, the adjustable gripper further includes one or more sensors configured to provide indication regarding the items to be gripped. In some embodiments, the sensors may include a proximity sensor and an RF ID reader.

According to some embodiments, the adjustable gripper may have at least two, at least three, at least four, at least five or at least six degrees of freedom. According to some embodiments, each of the arms of the adjustable gripper may have at least two, at least three, at least four, at least five, or at least six degrees of freedom.

According to some embodiments, characteristics of the item includes one or more of: type of item, size of item, weight of item, packaging of item, folding condition of item, number of items in a compartment, location of the item in the compartment, or any combination thereof.

According to some embodiments, the adjustable gripping of the item includes a gripping location/position of the item and/or the strength/tense of gripping.

According to some embodiments, the gripper assembly is located in close proximity to the back face of the container.

According to some embodiments, the degree of lateral movement of the set of compartments is at least partially based on the characteristic of items in the respective compartments.

According to some embodiments, the set of compartments is configured to laterally move closer to the back face of the container.

According to some embodiments, a coordinated movement of the gripper assembly and the set of compartments comprises a synchronized movement or consecutive movement.

According to some embodiments, the compartment size is adjustable, to allow precise accommodation of various types of items.

According to some embodiments, one or more of the compartments has one or more sensors configured to provide indications regarding inventory of items.

According to some embodiments, the system further includes at least one RF ID reader.

According to some embodiments, the RF ID reader includes an RF ID antenna positioned in close proximity to the dispensing outlet, configured to detect/identify a corresponding RF ID Tag of a dispensed item.

According to some embodiments, the system may further include an internal collection chamber configured to collect items that were gripped but were not dispensed via the dispensing outlet. According to some embodiments, items that were gripped but were not dispensed comprise: damaged items, items having a defective RF ID tag, items missing an RF Id tag, multiple gripped items, or any combination thereof.

According to some embodiments, the system may further include a disinfecting and/or cleaning unit. According to some embodiments, the disinfecting and/or cleaning unit may include one or more of: a UV disinfection unit, a microwave disinfecting unit, a vacuum unit, an air circulation unit, or any combination thereof. In some embodiments, the disinfecting unit/cleaning unit is located on the top portion of the system, for example, in the region of drawer 44, illustrated, for example, in FIG. 4.

According to some embodiments, the system may further include a lower back collecting chamber, configured to collect items that have been misplaced or fallen from various compartments.

According to some embodiments, the sets of compartments are arranged at a varying distance from the back face of the container.

According to some embodiments, the system may further include a user interface unit.

According to some embodiments, the system may further include one or more motors, one or more controllers, one or more processors, or combinations thereof.

According to some embodiments, the system may further include a communication unit.

According to some embodiments, the system may be functionally or physically associated with an item return unit.

According to some embodiments, the front face of the container and/or the back face of the container are configured to at least partially open, to allow placement of items in one or more compartments from a respective front side and/or a respective back side of the container.

According to some embodiments, a system with a back face optionally be opened is advantageous as it allows placement of the dispensing system in various environments, including, for example, sterile environments, in which the back side is placed in a non-sterile region, and the front face, from which the items are dispensed is located in a sterile environment (for example, a clean room or a sterile room). Such a setting allows the dispensing side to be kept sterile and clean and the back side to be accessible to a non-sterile environment.

According to some embodiments, there is provided an item dispensing system which includes:
- a container having a front face and a back face, the container includes:
- a plurality of storage compartments configured for storage/holding of items, wherein the storage compartments are arranged in one or more stationary sets, each set is arranged in rows and/or columns, wherein each of the sets of the storage compartments is placed in a varying distance from the back face of the container; and
- a gripper assembly configured to move along a vertical axis and/or a horizontal axis, said gripper assembly includes at least one adjustable gripper configured to allow an adjustable gripping of an item in a designated storage compartment and deliver the gripped item to a dispensing outlet, wherein the vertical and/or horizontal movement of the gripper assembly is configured to position the adjustable gripper over the designed compartment to allow the adjustable gripping of the item.

According to some embodiments, there is provided a method for dispensing an item from an item dispensing system, the method includes one or more of the steps of:

a) providing an item dispensing system which includes a container having a front face and a back face, the container includes: a plurality of storage compartments configured for storage/holding of items, wherein the storage compartments are arranged in sets, wherein each of the sets of the storage compartments is configured to move laterally between the front face and the back face of the container; and a gripper assembly configured to move along a vertical axis and/or a horizontal axis, the gripper assembly comprises at least one adjustable gripper configured to allow an adjustable gripping of an item in a designated storage compartment; and deliver the gripped item to a dispensing outlet; and b) selecting an item for dispensing using a user interface of the system;

wherein, based on the selected item, the lateral movement of the set of compartments and the horizontal and/or vertical movement of the gripper assembly is coordinated to allow temporal and spatial positioning of the adjustable gripper and the designed compartment comprising the selected item, to thereby allow the adjustable gripper to adjustably grip the selected item and deliver the selected item to the dispensing outlet.

According to some embodiments, the advantageous dispensing systems disclosed herein are user friendly, cost effective and environmentally friendly, as they consume less energy, they exhibit fast item dispensing/delivery time, requires less space, quite (less noise), have larger capacity, as the compartments may be filled to the top, have an increased variety of items, and the like.

According to some embodiments, the dispensing systems disclosed herein exhibit faster item dispensing time as compared to other dispensing systems. In some embodiments, the dispensing systems disclosed herein exhibit an (improvement of at least 50-60% in dispensing time), In the description and claims of the application, the words "include" and "have", and forms thereof, are not limited to members in a list with which the words may be associated.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods according to some embodiments may be described in a specific sequence, methods of the disclosure may include some or all of the described stages carried out in a different order. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. An item dispensing system comprising:
   a container having a front face and a back face, the container comprises:
   a plurality of storage compartments configured for storage/holding of items, wherein the storage compartments are arranged in one or more sets, each set is arranged in rows and/or columns, wherein each of the sets of the storage compartments is configured to move laterally between the front face and the back face of the container; and
   a gripper assembly configured to move along a vertical axis and/or a horizontal axis, said gripper assembly comprises at least one adjustable gripper configured to allow an adjustable gripping of an item in a designated storage compartment and deliver the gripped item to a dispensing outlet;
   wherein the lateral movement of the set of compartments and the movement of the gripper assembly is coordinated to thereby allow temporal and spatial accurate positioning of the adjustable gripper and the designed compartment.

2. The system according to claim 1, wherein the front face of the container and/or the back face of the container are configured to at least partially open, to allow placement of items in one or more compartments from a respective front side and/or a respective back side of the container.

3. The system according to any one of claim 1, wherein the sets of compartments are arranged at a varying distance from the back face of the container.

4. The system according to claim 1, further comprising a lower back collecting chamber, configured to collect items that have been misplaced or fallen from compartments.

5. The system according to claim 1, further comprising a disinfecting and/or cleaning unit, selected from: a UV disinfection unit, a microwave disinfecting unit, a vacuum unit, an air circulation unit, or any combination thereof.

6. The system according to claim 1, further comprising an internal collection chamber configured to collect items that were gripped but were not dispensed via the dispensing outlet, wherein items that were gripped but were not dispensed comprise: damaged items, items having a defective RF ID tag, Items missing an RF Id tag, multiple gripped items, or any combination thereof.

7. The system according to claim 1, wherein one or more of the compartments comprises one or more sensors configured to provide indications regarding inventory of items.

8. The system according to claim 1, wherein a coordinated movement of the gripper assembly and the set of compartments comprises a synchronized movement or a sequential movement.

9. The system according to claim 1, wherein the degree of lateral movement of the set of compartments is at least partially based on the characteristic of items in the respective compartments.

10. The system according to claim 1, wherein the gripper assembly is located in close proximity to the back face of the container.

11. The system according to claim 1, wherein the adjustable gripper comprises at least two opposing movable arms, configured to adjustably grip an item, based on the characteristics of the item in the compartment.

12. The system according to claim 11, wherein the characteristics of the item comprises one or more of: type of item, size of item, weight of item, packaging of item, folding condition of item, number of items in a compartment, location of the item in the compartment, or any combination thereof.

13. The system according to claim 12, wherein the adjustable gripping of the item comprises a gripping location/position of the item and/or the strength/tense of gripping.

14. The system according to claim 1, functionally or physically associated with an item return unit.

15. The system according to claim 14, wherein the return unit comprises a compactor, configured to compress returned items within the return unit.

16. The system according to claim 15, wherein operation of the compactor is controlled by a processor, periodically, or based on information obtained from one or more sensors indicative of amount, size and/or weight of returned items.

17. A method for dispensing an item from an item dispensing system, the method comprising:
a) providing an item dispensing system comprising:
  a container having a front face and a back face, the container comprises:
  a plurality of storage compartments configured for storage/holding of items, wherein the storage compartments are arranged in sets, wherein each of the sets of the storage compartments is configured to move laterally between the front face and the back face of the container; and
  a gripper assembly configured to move along a vertical axis and/or a horizontal axis, the gripper assembly comprises at least one adjustable gripper configured to allow an adjustable gripping of an item in a designated storage compartment; and deliver the gripped item to a dispensing outlet;
b) selecting an item for dispensing using a user interface of the system;
wherein, based on the selected item, the lateral movement of the set of compartments and the horizontal and/or vertical movement of the gripper assembly is coordinated to allow temporal and spatial positioning of the adjustable gripper and the designed compartment comprising the selected item, to thereby allow the adjustable gripper to adjustably grip the selected item and deliver the selected item to the dispensing outlet.

18. An item dispensing system, comprising:
a plurality of storage compartments configured for storage/holding of items, wherein the storage compartments are arranged in rows and/or columns;
at least two gripper units configured to move along at least one axis, each of said gripper units being configured to grip an item positioned within a designated storage compartment and deliver the gripped item to a dispensing outlet of said item dispensing system;
  wherein said at least one axis and/or one of said at least two gripper units are configured such that said at least two gripper units are independently operable, thereby allowing concurrent dispensing of two or more items, wherein each of said items originates from a separate designated storage compartment; and
a disinfecting and/or cleaning unit.

19. The item dispensing system of claim 18, comprising a user interface module configured to receive input from a user associated with a specified item to be dispensed, and where said processor is configured to identify a storage compartment containing said specified item.

20. The item dispensing system of claim 18 wherein the disinfecting and/or cleaning unit comprises one or more of: a UV disinfection unit, a microwave disinfecting unit, a vacuum unit, an air circulation unit, or any combination thereof.

21. The item dispensing system of claim 18, wherein the storage compartments are arranged in one or more stationary sets, each set is arranged in rows and/or columns, wherein each of the sets of the storage compartments is placed in a varying distance from a back face of a container comprising said storage compartments.

22. The item dispensing system of claim 18, wherein said grippers are concurrently or consecutively movable along said at least one axis.

23. The item dispensing system of claim 18, wherein said grippers are moveably coupled to said at least one axis.

24. The item dispensing system of claim 18, wherein said at least one axis comprises at least one horizontal axis and/or at least one vertical axis.

25. The item dispensing system of claim 18, comprising a processor and a driving unit in communication with said processor, wherein said driving unit is coupled to said at least two grippers and said processor is configured to control a movement of said at least two grippers by controlling an operation of said driving unit.

26. The item dispensing system of claim 25, wherein said processor is configured to calculate an operation rout for two or more gripper units simultaneously.

27. The item dispensing system according to claim 18, functionally or physically associated with an item return unit.

28. The item dispensing system according to claim 27, wherein the return unit comprises a compactor, configured to compress returned items within the return unit.

* * * * *